United States Patent
Carrara

(10) Patent No.: US 6,231,885 B1
(45) Date of Patent: May 15, 2001

(54) COMPOSITION FOR CONTROLLED AND SUSTAINED TRANSDERMAL ADMINISTRATION

(75) Inventor: Dario Carrara, Buenos Aires (AR)

(73) Assignee: Permatec Technologie AG (CH)

( * ) Notice: Subject to any disclaimer, the term of this patent is extended or adjusted under 35 U.S.C. 154(b) by 0 days.

(21) Appl. No.: 09/153,798

(22) Filed: Sep. 15, 1998

(30) Foreign Application Priority Data

Sep. 17, 1997 (IT) .............................................. MI97A2106

(51) Int. Cl.[7] ....................................................... A61F 13/02
(52) U.S. Cl. .............................. 424/448; 424/449; 602/41; 602/60; 604/290; 604/304; 604/307
(58) Field of Search ...................................... 424/448, 449; 602/41, 60; 604/290, 304, 307

(56) References Cited

U.S. PATENT DOCUMENTS

| | | |
|---|---|---|
| 4,764,381 | 8/1988 | Bodor et al. . |
| 4,863,970 | 9/1989 | Patel et al. . |
| 5,023,084 | 6/1991 | Chien et al. . |
| 5,378,473 | 1/1995 | Sharma et al. . |
| 5,466,465 | 11/1995 | Royds et al. . |

FOREIGN PATENT DOCUMENTS

| | | |
|---|---|---|
| 0171742 | 2/1986 | (EP) . |
| 0279977 | 8/1988 | (EP) . |
| 0279982 | 8/1988 | (EP) . |
| 0376534 | 7/1990 | (EP) . |
| 0413553 | 2/1991 | (EP) . |
| 0519926 | 12/1992 | (EP) . |
| 0551349 | 7/1993 | (EP) . |
| 0573133 | 12/1993 | (EP) . |
| 9011064 | 10/1990 | (WO) . |
| 9312744 | 7/1993 | (WO) . |
| 9325168 | 12/1993 | (WO) . |
| 9501767 | 1/1995 | (WO) . |
| 9529678 | 11/1995 | (WO) . |

OTHER PUBLICATIONS

Development Concepts and Practice in TTS, 1987, pp. 22–81, "Transdermal Controlled Systemic Medications", Yie W. Chien.

Journal of Controlled Release, vol. 25, No. 1/02, May 27, 1993, pp. 1–20, Santus G C et al., "Transdermal Enhancer Patent Literature".

Journal of Controlled Release, vol. 29, No. 1/02, Feb. 1, 1994, pp. 177–185, Kenju Sugibayashi et al., "Polymers for Transdermal Drug Delivery Systems".

Pharmazie, vol. 51, No. 9, Sep. 1, 1996; pp. 619–637, Kalbitz J et al., "Modulation der Wirkstoffpenetration in Die Haut".

Primary Examiner—S. Mark Clardy
Assistant Examiner—Michael A. Williamson
(74) Attorney, Agent, or Firm—Hedman & Costigan, PC

(57) ABSTRACT

A patch for transdermal administration of drugs through controlled release system, consisting essentially of:
 A) a flexible backing layer;
 B) an adhesive layer comprising:
  an adhesive pressure sensitive adhesive polymeric matrix,
  a cohesion improver,
  a tackifier agent,
  a combination of permeation enhancers consisting of a first component which is a saturated fatty acid or fatty alcohol represented by the formula $CH_3-(CH_2)_n-COOH$ or $CH_3-(CH2)_n-CH_2OH$ respectively, in which n is an integer from 6 to 16, and of a second component which is a monounsaturated fatty acid or fatty alcohol represented by the formula $CH_3-(C_nH_{2(n-1)})-COOH$ or $CH_3-(C_nH_{2(n-1)})-CH_2OH$ respectively, in which n is an integer from 8 to 22, with the provision that the chain lenght of the first component is different from that of the second component,
 C) a protective liner, which is removed at the moment of use.

4 Claims, 14 Drawing Sheets

Graphic 1

Graphic 2

Graphic 7

Graphic 8

Graphic 9

Graphic 10

Graphic 11

Graphic 12

Graphic 17

Graphic 18

Graphic 20

Graphic 21

Graphic 22

Graphic 23

Graphic 24

COMPOSITION FOR CONTROLLED AND SUSTAINED TRANSDERMAL ADMINISTRATION

This application claims priority of Italian Application Serial No. MI97A 002106, filed Sept. 17, 1997.

FIELD OF THE INVENTION

The present invention relates to a novel composition for controlled and sustained drug transdermal administration, comprising a combination of two or more fatty acids or alcohols of different chain length as permeation enhancers.

The invention reveals a monolithic formulation with good adhesive properties and low irritation potential, useful for administering active agent(s) by transdermal route, during long periods of time. A formulation that administers active agent(s) or a combination thereof, at a permeation rate that would ensure therapeutically effective systemic concentration. This formulation contains defined amounts of chemicals that minimize the barrier characteristics of the uppermost layer of the epidermis and provide sustained and controlled permeation rate. Said chemicals are: fatty acids such as oleic acid, palmitoleic acid, palmitic acid, myristic acid, lauric acid, etc. and fatty alcohols such as oleyl alcohol, palmityl alcohol, myristyl alcohol, lauryl alcohol, n-decanol, etc. This formulation contains defined amounts of chemicals that assure good adhesive properties and low irritation potencial during long periods of time.

BACKGROUND OF THE INVENTION

While there are many patents and publications available which relate to the transdermal administration of drugs, and the use of penetration enhancers, the applicant is unaware of any prior art which relates to the penetration enhancer composition of a monolithic transdermal device with adequate adhesive properties disclosed herein and to use such composition in the transdermal administration of drug(s).

The present invention relates to a novel composition based on enhancers combination, specifically fatty acids and fatty alcohols with different chain length in an adhesive matrix containing defined amount of chemicals as cellulose derivatives (ethylcellulose) to avoid cohesive failure. This formulation is suitable for transdermal administration of drug(s) alone or mixture thereof, and would provide therapeutically useful concentrations of drug for long periods of time, up to 7 (seven) days.

Using skin as the port for the drug entry offers unique potential, because transdermal delivery permits close control over drug absorption. For example, it avoids factors that can cause unpredictable absorption from the gastrointestinal tract, including: changes in acidity, motility, and food content. It also avoids initial metabolism of the drug by the liver. Thus, controlled drug entry through skin can achieve a high degree of control over blood concentrations of drug.

Transdermal delivery particularly benefits patients with chronic diseases. Many of such patients have difficulties following regimen requiring several daily doses of medications that repeatedly cause unpleasant symptoms. They find the same drugs much more acceptable when administered in transdermal systems that require, application infrequently, in some cases, only once or twice a week and that reduce adverse events.

Monolithic transdermal drug delivery systems involve incorporation of an active agent into the pressure sensitive adhesive formulation. The pressure sensitive adhesive must adhere effectively to the skin and then permit migration of the drug from the pressure sensitive adhesive through the skin and into the blood stream of the patient. Transdermal administration of drugs offers several therapeutic and compliance advantages over the more traditional routes of administration. A major drawback of this therapy however, is the limitation of the amount of drug that can be transported across the skin. This limitation is due to several factors. Since the skin is a protective barrier by nature, the rates of transport of most compounds through the skin is quite slow.

The rate of percutaneous absorption can be affected by the oil/water partition coefficient, the polarity of the drug and its degree of ionization, its solubility characteristic, molecular weight, volatility, concentration and the nature of the drug vehicle.

In order to overcome the barrier properties of the stratum corneum and facilitate the percutaneous absorption of the active agent, many compounds are described as penetration enhancers, such as, azone, glycol, pyrrolidone, fatty alcohol, fatty acid and ester thereof, etc., mentioned by Møllgaard in "Pharmaceutical Skin Penetration Enhancement", Marcel Dekker, New York 1993, pages 229–242.

The behavior of an enhancer depends on the penetrant drug and the transdermal device design. That is, a given enhancer does not necessarily increase the absorption of all drugs, as it is quoted by Hori, Satoh and Maibach in "Percutaneous Absorption", Marcel Dekker, New York 1989, pages 197–211.

It is possible to excerpt from the scientific literature many examples in which two or more permeation enhancers in mixture have been shown to act synergically in percutaneous absorption enhancement.

A true synergically effect is achieved when the combination of permeation enhancers elicit a greater effect than the addition of the individual responses of each component used alone. However, for practical reasons the definition is expanded to comprise all examples for which two or more permeation enhancers in a mixture have worked well together in increasing the transport of drugs into and through the skin.

Cooper (1984) showed that the combination of propylene glycol and oleic acid increased the penetration of salicylic acid compared with each penetration enhancer alone. Aungst et al (1986) showed that the effects of permeation enhancer on absorption of naloxone in in vitro studies are vehicle dependent, showing that the combination of vehicles promotes the absorption better than one vehicle alone.

Green, Guy and Hadgraft (1988) reported that oleic and lauric acid can be employed to increase the permeability of human skin to a number of charged and uncharged molecules. The authors suggest that improved permeation is due to disruption of the stratum corneum structure.

Fatty acids are described as effective penetration enhancers for the transdermal delivery of several drugs. Golden et al. (1987) postulated that the likely enhancement mechanism of the fatty acids is mediated by the disruption of the stratum corneum lipid packed and hence decrease the diffusional resistance to permeants.

On the contrary Kadir et al. in "Pharmaceutical Skin Penetration Enhancement", Marcel Dekker, New York 1993, pages 215–227, assert that the mode of action of some enhancers is still unclear since, in most studies, no efforts have been made to distinguish between their direct effect on the skin barrier properties on the one hand, and their effects on the thermodynamic activity of the penetrating species in the vehicle on the other. It is quite likely that incorporating permeation enhancer in transdermal formulations will change the thermodynamic activity of the drug in the matrix, and thereby lead to a positive or negative "push" effect. In addition, some permeation enhancers may conceivable penetrate into the highly ordered intercellular lipid structure of the stratum corneum and reduce its resistance by increasing lipid acyl chain mobility, thus providing a "pull" effect.

It is now well accepted that the mechanism by which fatty acids and alcohols increase the skin permeability involves an interaction with the intercellular lipids in the stratum corneum. Alteration of the lipid bilayers has been assessed using differential scanning calorimetry (DSC) and fourier infrared spectroscopy (FTIR). These methods indicate that the enhancer system may cause a disruption of the ordered lamellar structure of the biolayers in the stratum corneum, leading to an increased fluidization of intercellular medium. As it is stated by Møllgaard in "Pharmaceutical Skin Penetration Enhancement", Marcel Dekker, New York 1993, pages 229–242 it is likely that in a binary composition comprising oleic acid and propylene glycol, the propylene glycol enhances the oleic acid penetration, and oleic acid promotes the propylene glycol permeation. This mutual effect could thus result in a more rapid diffusion of the drug molecules across the skin.

The monolithic transdermal system, is a system incorporating a backing layer, a matrix layer and a release liner. The matrix layer is made of an adhesive polymer material in which the drug is dissolved or dispersed and the rate at which the drug is released from the device, is controlled by the diffusion within the polymer matrix following the Fick's law of diffusion.

This type of transdermal drug delivery system is exemplified by the development and marketing of nitroglycerin transdermal therapeutic system (Minitran by 3M) or estradiol (Climara by 3M) which have been approved by the FDA.

After a careful search looking for relevant documents to the present invention we become aware that the scientific information related to how the permeation enhancer(s) release from the transdermal systems to the skin, is scarce. Since only EP 0 279 982 describes a transdermal drug delivery system for administering contraceptives and codelivering of glycerol monooleate as permeation enhancer, to aid in drug delivery across the skin. In this patent application it is shown some results describing the release profile of glycerol monooleate.

EP 0 519 926 B1 discloses a transdermal delivery system, from which the release rate of the active agent is controlled by the dissociation of an inclusion complex of the active agent in a drug depot (cyclisized polysaccharide).

WO 93/25168 describes a transdermal drug delivery system which utilizes glycerine for moderating and controlling the delivery of drugs across biological membranes.

U.S. Pat. No. 5,466,465 discloses about a transdermal drug delivery system in which the drug granules are encapsulated within the material which controls the release over time of an active agent.

EPA 0 413 553 reveals a transdermal drug delivery in which drug delivery is biphasic. That is the drug is delivered at a therapeutically effective rate during an initial delivery phase, followed by a secondary phase in which no drug is delivered.

EPA 0 573 133 claims a transdermal device containing gestoden combined with one or more estrogens. The incorporation of penetration enhancer is also disclosed.

EPA 0 279 977 describes a transdermal device for administering progesterone and an estradiol ester alone or in combination, utilizing a polymer matrix which has the drug(s) with a penetration enhancer such as sucrose monococoate, glycerol monooleate, sucrose monolaurate, glycerol monolaurate, etc.

U.S. Pat. No. 5,023,084 claims a transdermal estrogen/progestin device comprising a polymeric layer made from polymer adhesive such as polyacrylic, silicone or other suitable polymer adhesives and n-decyl alcohol or capric acid as penetration enhancers.

WO 90/11 064 discloses a skin penetration enhancer composition for estrogen and progestin or a mixture thereof. The composition contains diethylene glycol monoethyl or monomethyl ether in addition to propylene glycol monolaurate, methyl laurate or the like.

U.S. Pat. No. 4,764,381 discloses a pharmaceutical preparation to obtain transdermal delivery of drug utilizing 2-ethyl-1, 3-hexanediol alone an/or in combination with oleic acid.

EP 0 551 349 claims the use of high boiling point solvents (in excess of 110° C.) suitable for forming saturated or supersaturated solutions of the active agent in the transdermal device, such as propylene glycol, diethylene glycol, glycerol, fatty alcohols, fatty acids, esters, triglycerides, etc.

U.S. Pat. No. 4,863,970 discloses a binary penetration enhancement combination comprising oleic acid, oleyl alcohol or glycerol esters of oleic acid combined with lower alcohols.

U.S. Pat. No. 5,378,473 claims the use of ester of the formula $[CH_3(CH_2)_mCOO]_nR$, preferably propylene glycol monolaurate (PGML) and glycerol monooleate (GMO) as permeation enhancer in the transdermal administration of short or intermediate half-life benzodiazepines.

WO 95/01767 describes a monolithic matrix formulations for the transdermal administration of ketorolac tromethamine and molsidomine, also the inclusion of propylene glycol monolaurate (PGML) and propylene glycol (PG) as permeation enhancers is disclosed.

None of the above mentioned inventions or publications report a combination of fatty acids and/or fatty alcohols, such as oleic acid and lauric acid, oleic acid and lauryl alcohol, oleyl alcohol and lauric acid or oleyl alcohol and lauryl alcohol, in a transdermal monolithic device, with good adhesive properties and low irritation potential by means of the addition of a cohesive improver such as ethylcellulose and adequate tackifier resins, designed to administer active agent(s) or mixture thereof by the transdermal route.

The specific literature does not describe the addition of some "cohesion improver", as it is disclosed in the present invention. Typically, adding enhancers to PSA will plasticize the PSA and lower their shear strength. The reduction in shear resistance may result in adhesive residue on the skin, edge lifting of the patch during wear (cohesion failure), or loss of adhesion. The recovery of the tack and the adhesion can be made by addition of some tackifier agents as it is disclosed in the literature (Satas D., chapter 4: Tack, in Handbook of pressure sensitive adhesive technology, N. York 1989, pp. 38–60).

Chien in "Transdermal Controlled Systemic Medications", Marcel Dekker, New York 1987, pages 25–81, concludes that the efficacy of skin penetration enhancer for a specific active agent, is function of the type, concentration and, how the penetration enhancer release from the devices.

The prior art presented herein clearly proves that for some active agents, as shown in the present patent application, the penetration enhancer composition and the adequate controlled permeation rate across the skin can be achieved only by the careful investigation of multiple variables. Although prior art was useful for the theoretical approach.

SUMMARY OF THE INVENTION

The present invention provides a novel formulation of a monolithic transdermal device comprising:
a) a flexible backing; and
b) an adhesive layer comprising an homogeneous mixture of:
   i) a pressure sensitive adhesive polymeric matrix; and
   ii) cohesive improver, and
   iii) a tackifier resin; and
   iv) a combination of fatty acids and/or fatty alcohols as permeation enhancers, and
   v) one or more drugs, and
   vi) carriers or drug vehicles, antioxidants, preservatives, etc.
c) a protective liner, which is removed at the time of use.

It has been surprisingly discovered that it is possible to achieve a therapeutically effective, sustained and controlled penetration rate of active agent(s) into the skin with the aid of the inventive means.

A monolithic patch formulation which provides a therapeutically effective transdermal delivery of active agent, is claimed.

It has been discovered surprisingly that the formulation discloses herein, provides sustained and controlled active agent permeation rate for long periods of time, up to 7 (seven) days.

Surprisingly it has been discovered that in the administration of several active agents, the combination of oleic acid and lauric acid acts as the most adequate enhancer composite.

It has been found that when fatty acids and/or fatty alcohols are combined as permeation enhancers, a sustainable active agent(s) permeation rate occurs during all patch application time.

Surprisingly it has been found that a combination of one or more fatty acids and/or one or more fatty alcohols with different chain lengths, as permeation enhancer in monolithic transdermal device, provides sustained and controlled drug permeation rates.

Surprisingly, it has been found that a great proportion of the amount of lauric acid is delivered at early times, generating a "pull" effect; and oleic acid is delivered in small amount and is prone to remain in the adhesive monolithic matrix, generating specially "push" effect.

Surprisingly, it has been found that the addition of ethylcellulose acts as efective cohesive improver, recovering good physical properties to the adhesive formulation. The maintenance of adequate adhesive physical properties is particularly important for the design of patches to be used for long periods of time up to 7 (seven) days.

DESCRIPTION OF THE DRAWINGS

The FIG. 1 represents the schematic front view of the apparatus 5 USP 23 (1995), used for analyzing the enhancer release, wherein 1 is the chamber, 2 is the paddle and 3 is the disk.

The FIG. 2 represents the schematic front view of the diffusion chamber, (Hanson P/N 57-VC vertical diffusion cell), used for determining the in vitro drug permeation through abdominal guinea pig skin, wherein 1 is the water jacket, 2 the top plate, 3 the donor chamber, 4 the dosage wafer, 5 the clamp, 6 the membrane, 7 the sample point, 8 the stirring helix, 9 the magnetic stirrer, 10 the media replace tube, 11 the sample tube, 12 the sample from microette, 13 the cell level line and 14 the cell receptor.

Figure 3:
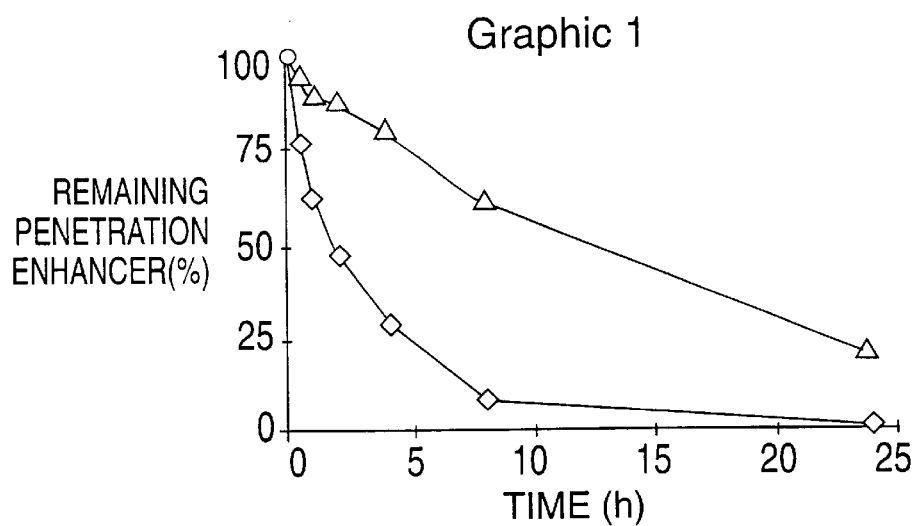
Figure 3:
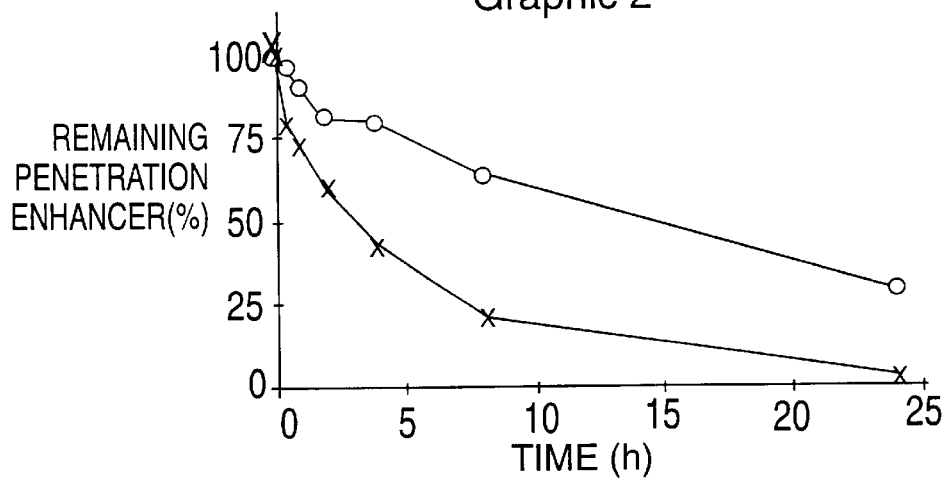

In Graphic 1 of FIG. 3 are represented the values of remaining penetration enhancers containing lauric acid and oleic acid (% by weight), vs. time, obtained in in vitro experiments from transdermal patches, which adhesive matrix is described in Example 1 (see table I and II).

In Graphic 2 of FIG. 3 are represented the values of remaining lauric acid and oleic acid (% by weight) vs. time, obtained in in vitro experiments from transdermal patches, which adhesive matrices are respectively described in Examples 2 and 3 (see table I and II).

Figure 4:
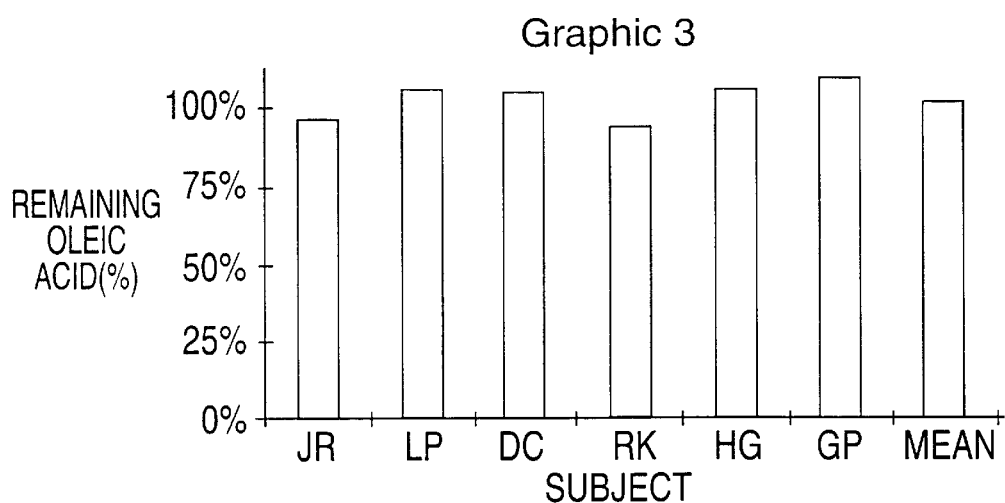
Figure 4:
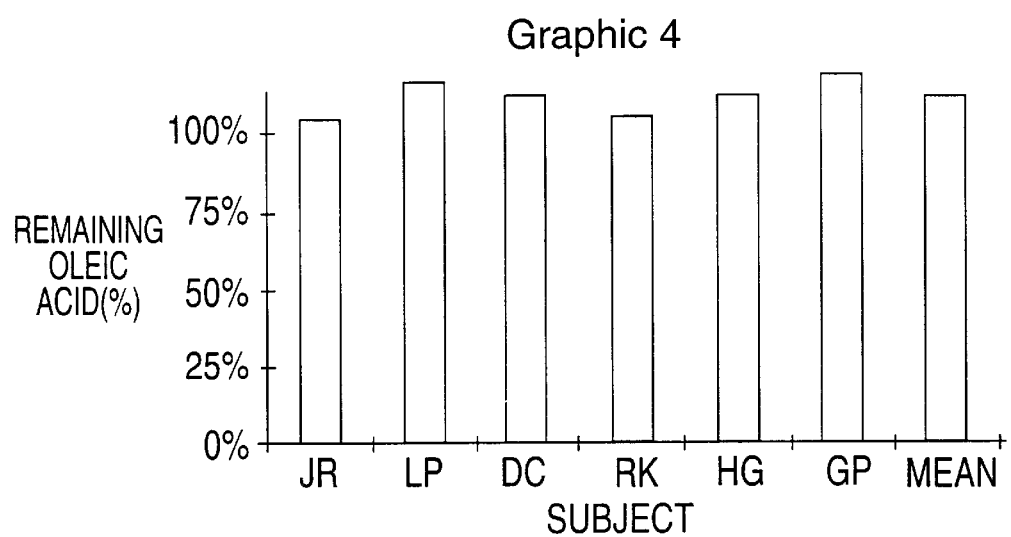

In Graphic 3 of FIG. 4 are depicted the individual and mean values of remaining oleic acid (% by weight), obtained in in vivo experiments from transdermal patches, which adhesive matrix is composed as in Example 1 (see table III).

In Graphic 4 of FIG. 4 are depicted the individual and mean values of remaining oleic acid (% by weight), obtained in in vivo experiments from transdermal patches, which adhesive matrix is described in Example 3 (see table III).

Figure 5:
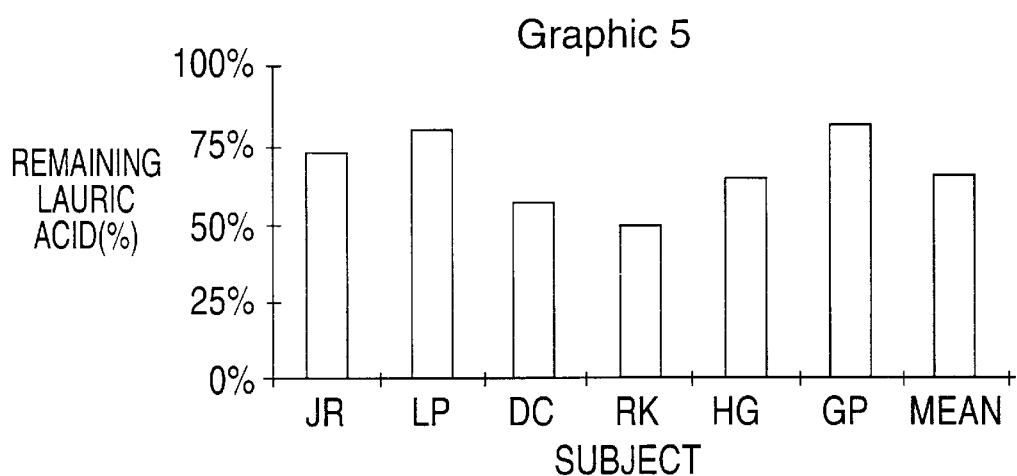
Figure 5:
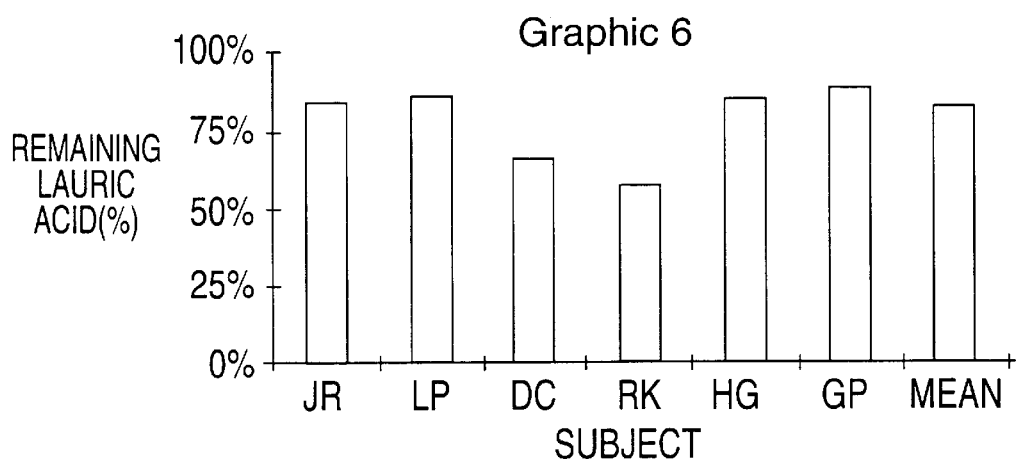

In Graphic 5 of FIG. 5 are depicted the individual and mean values of remaining lauric acid (% by weight), obtained in in vivo experiments from transdermal patches, which adhesive matrix has the composition described in Example 1 (see table III).

In Graphic 6 of FIG. 5 are depicted the individual and mean values of remaining lauric acid (% by weight), obtained in in vivo experiments from transdermal patches, which adhesive matrix has the composition described in Example 2 (see table III).

Figure 6:
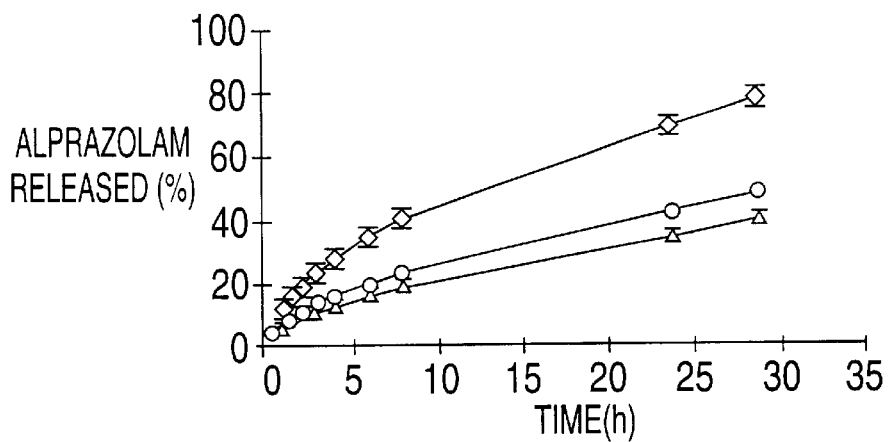
Figure 6:
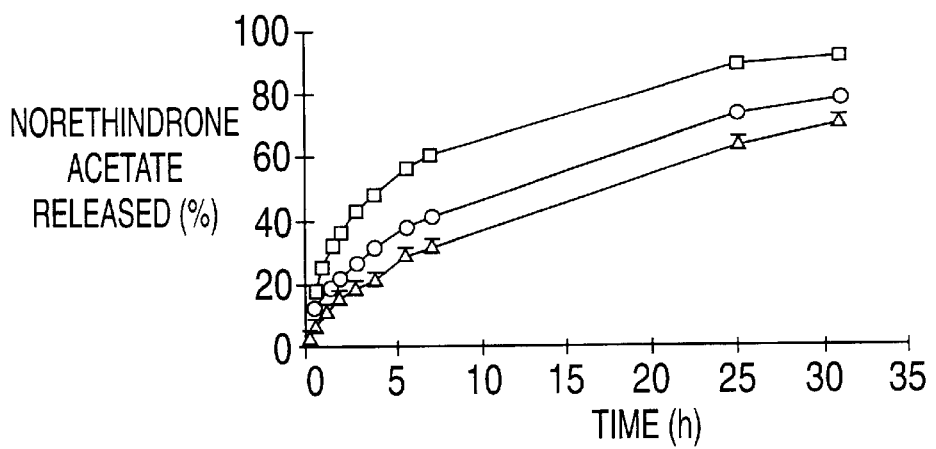

Graphic 7 of FIG. 6 illustrates the alprazolam released (%) vs. time (h), obtained in in vitro experiments from transdermal patches, which adhesive matrices are respectively described in Example 11 Δ, in Example 12 ○ (OA), and in Example 13 ◇ (OA/LA), see table IV.

Graphic 8 of FIG. 6 illustrates the norethindrone acetate released (%) vs.time (h), obtained in in vitro experiments from transdermal patches, which adhesive matrices have the compositions described in Example 4 □ (OA/LA), in Example 7 ○ (OA), and in Example 10 Δ (see table V).

Figure 7:
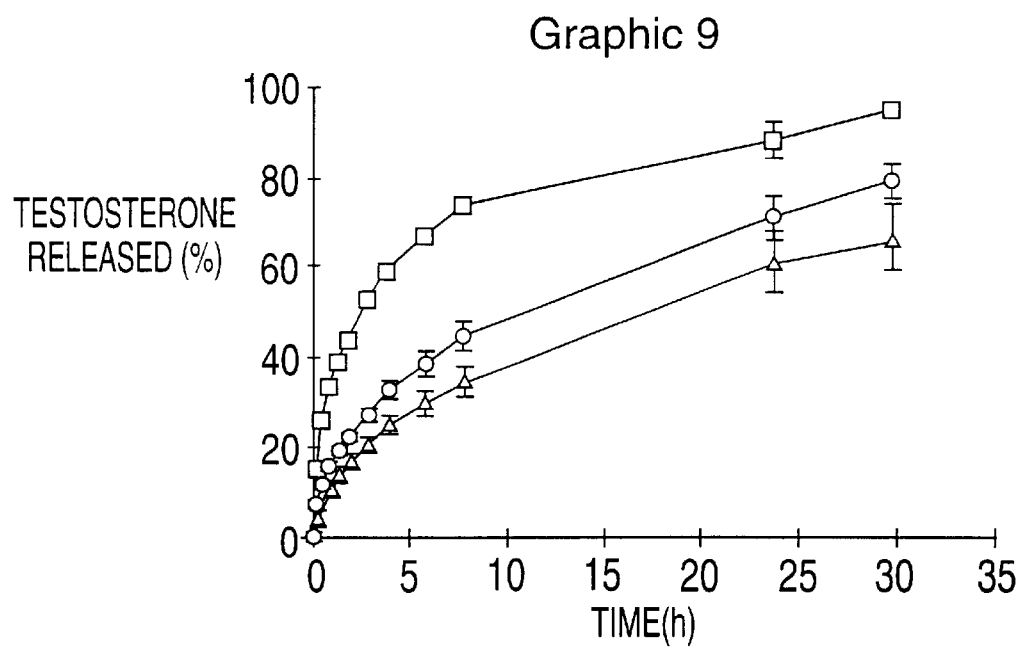
Figure 7:
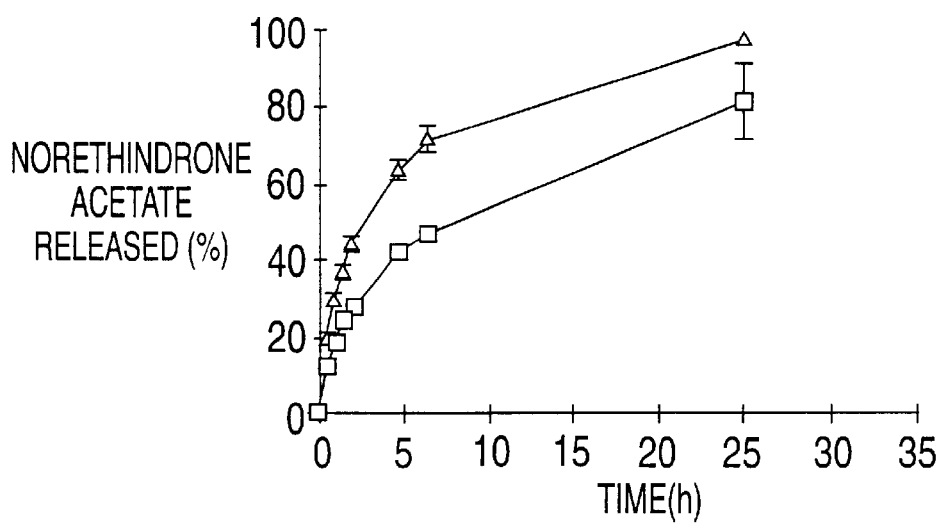

Graphic 9 of FIG. 7 illustrates the testosterone released (% by weight) vs.time (hours) in vitro experiments carried out with transdermal patches, which adhesive matrices have the compositions described in Example 14 □ (OA/LA), in Example 15 Δ and in Example 16 ○ (OA), see table VI.

Graphic 10 of FIG. 7 illustrates the norethindrone acetate released (% by weight) vs. time (h), obtained in in vitro experiments with transdermal patches, which adhesive matrices are those described in Example 18 Δ (OAL/LAL) and in Example 19 □ (OA/LA), see table VII.

Figure 8:
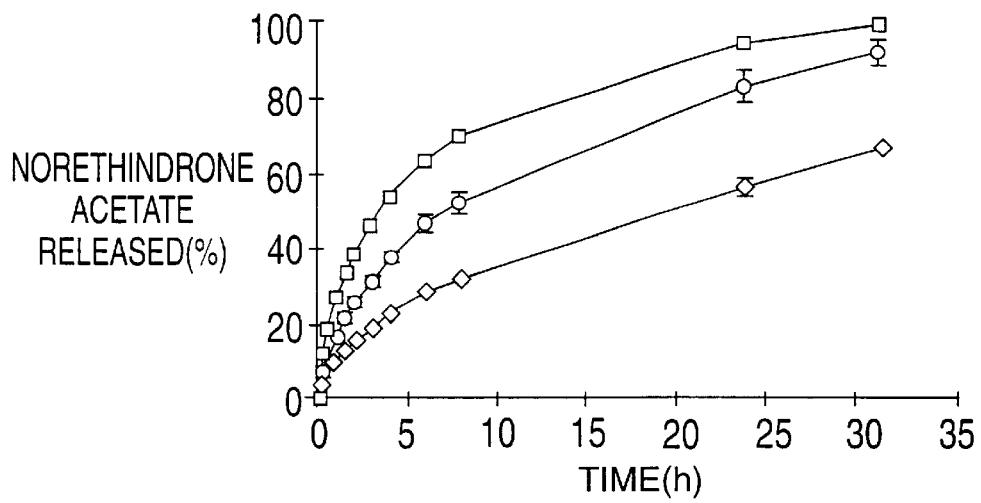
Figure 8:
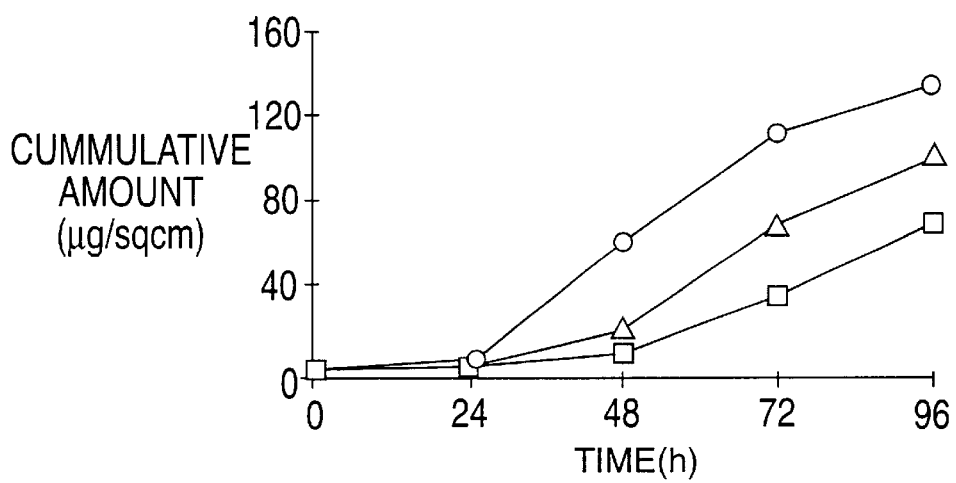

Graphic 11 of FIG. 8 illustrates the norethindrone acetate released (% by weight) vs. time (h), obtained in in vitro experiments from transdermal patches, which adhesive matrices are those in Example 20 ◇, in Example 21 ○ (OAL), and in Example 22 □ (OAL/LA), see table VIII.

Graphic 12 of FIG. 8 illustrates the concentration of estradiol permeated (cumulative amount in $\mu g/cm^2$) vs.time (h), obtained in in vitro experiments from transdermal patches, which adhesive matrices are described in Example 4 ● (LA/OA), in Example 5 ■ (GMO) and in Example 6 ▲ (GML), see table IX.

Figure 9:
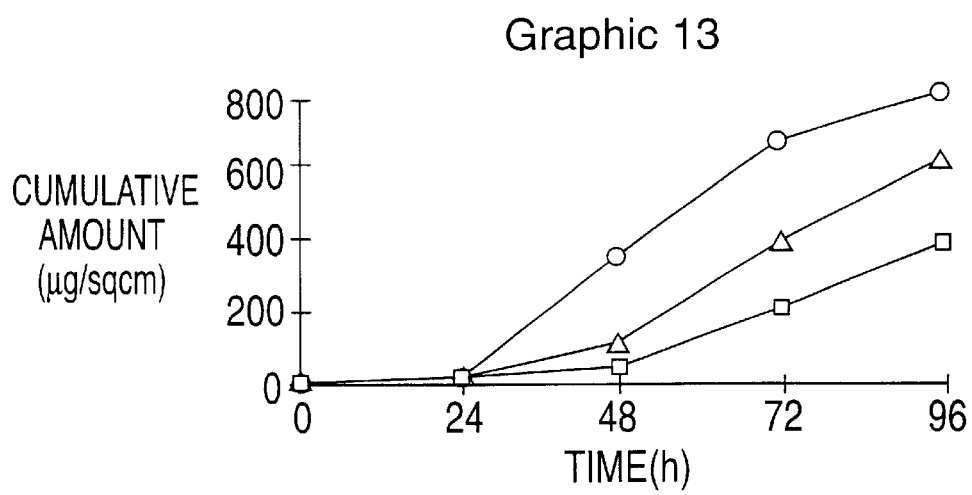
Figure 9:
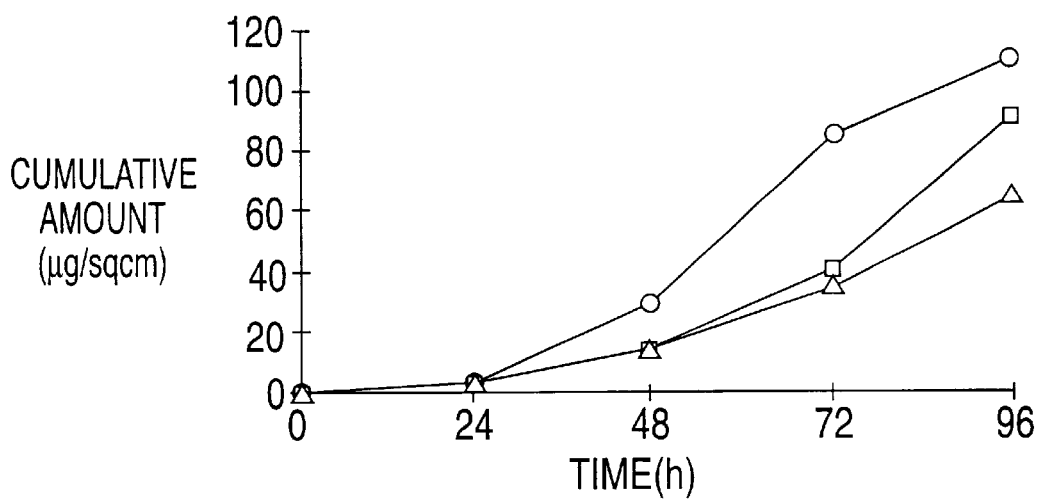

Graphic 13 of FIG. 9 illustrates the concentration of norethindrone acetate permeated ($\mu$g/cm$^2$) vs. time (h), obtained in in vitro experiments carried out with transdermal patches, which adhesive matrices have the compositions described in Example 4 ● (OA/LA), in Example 5 ■ (GMO) and in Example 6 ▲ (GML), see table X.

Graphic 14 of FIG. 9 illustrates the concentrations of estradiol permeated ($\mu$g/cm$^2$) vs. time (h), obtained in in vitro experiments carried out with transdermal patches, which adhesive matrices are those in Example 4 ● (OA/LA), in Example 8 ■(IPM) and in Example 9 ▲(GMDC), see table XI.

Figure 10:
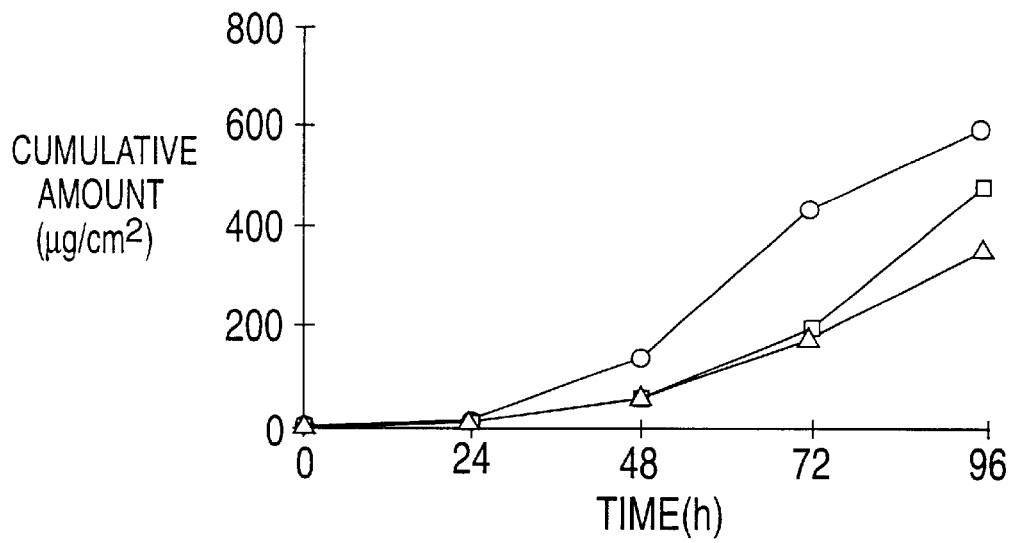
Figure 10:
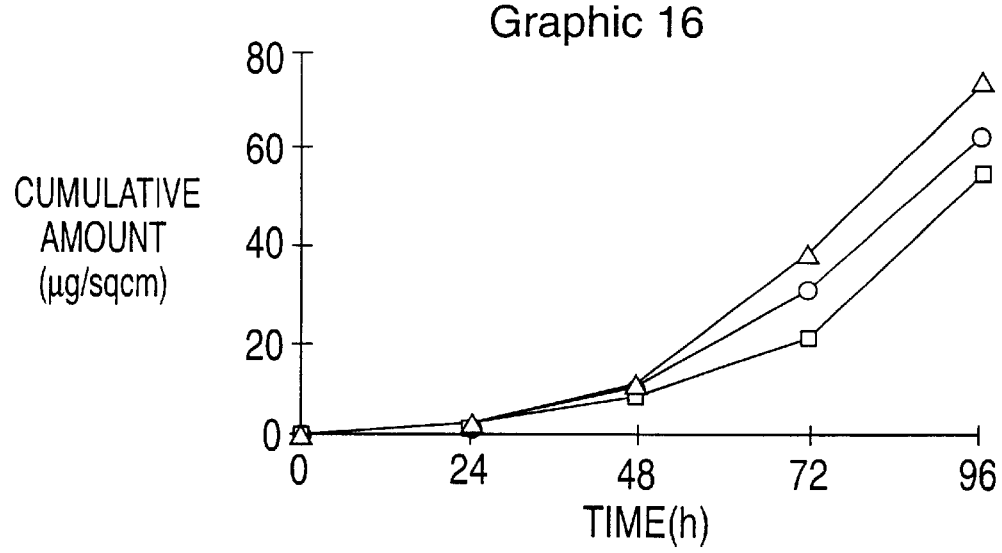

Graphic 15 of FIG. 10 illustrates the concentration of norethindrone acetate permeated ($\mu$g/cm$^2$) vs.time (h), obtained in in vitro experiments carried out with transdermal patches, which adhesive matrices have the compositions described in Example 4 ● (OA/LA), in Example 8 ■ (IPM) and in Example 9 ▲ (GMDC), see table XII.

Graphic 16 of FIG. 10 illustrates the concentration of estradiol permeated ($\mu$g/cm$^2$) vs.time (h), obtained in in vitro experiments with transdermal patches, which adhesive matrices have the compositions described in Example 4 ● (OA/LA), in Example 17 ■ (OAL/LA) and in Example 18 ▲ (GMDC), see table XIII.

Figure 11:
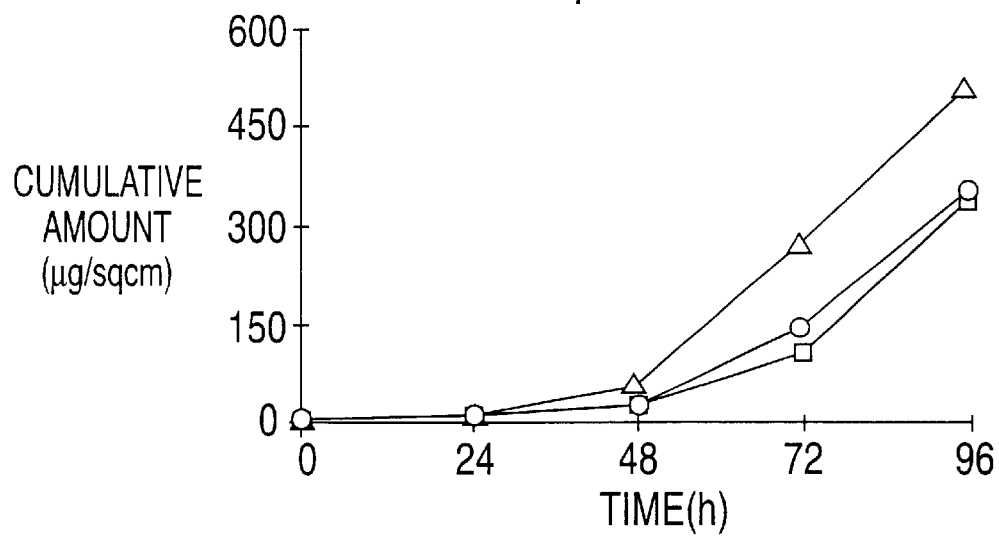
Figure 11:
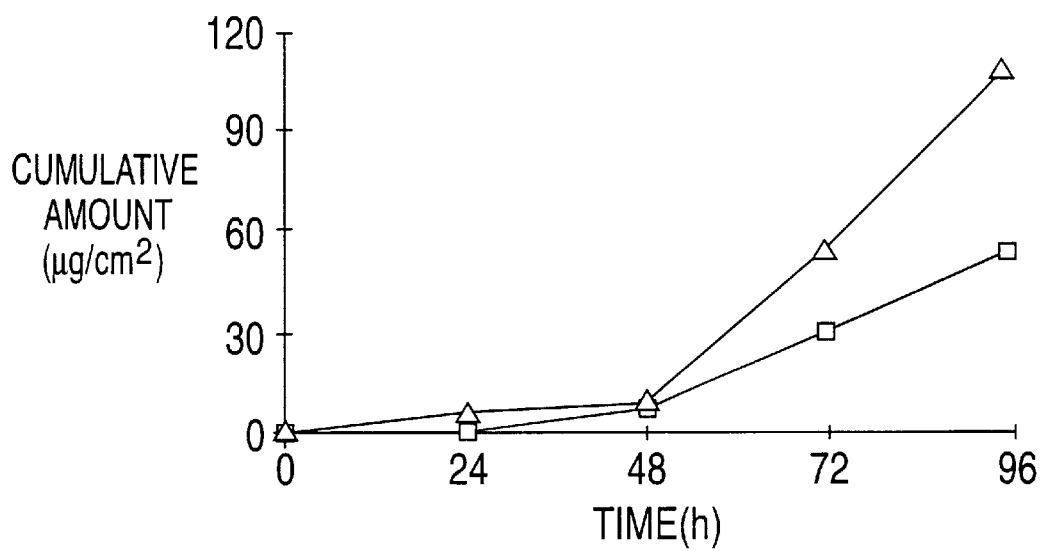

In Graphic 17 of FIG. 11 the concentration of norethindrone acetate permeated ($\mu$g/cm$^2$) vs. time (h), is illustrated, said concentration resulting in in vitro experiments from transdermal patches, which adhesive matrices are those in Example 4 ● (OA/LA), in Example 17 ■ (OAL/LA) and in Example 18 ▲ (OAL/LAL), see table XIV.

In Graphic 18 of FIG. 11 the concentration of estradiol permeated ($\mu$g/cm$^2$) vs.time (h), is illustrated, said concentration resulting from transdermal patches, which adhesive matrices have the compositions described in Example 4 Δ (OA/LA) and in Example 7 □ (OA), table XV.

Figure 12:
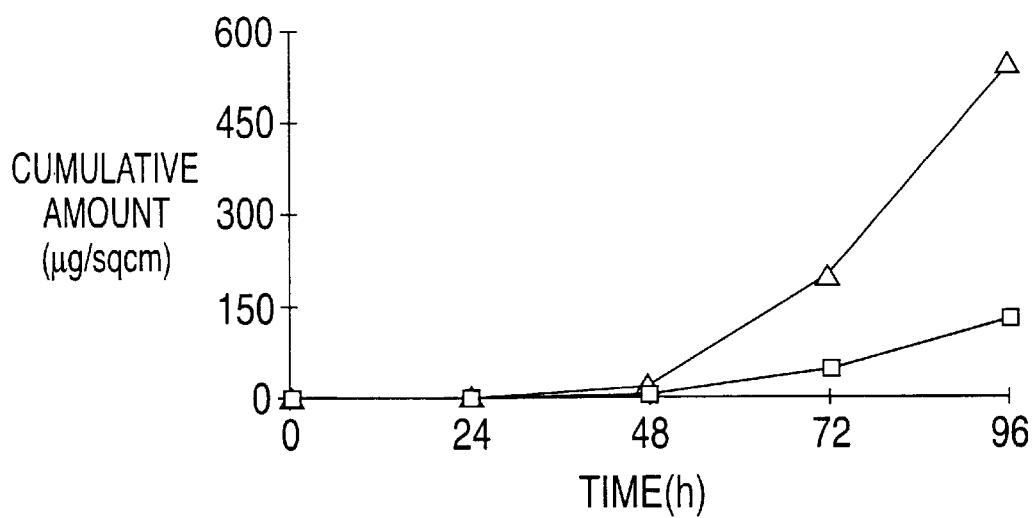

Graphic 19 of FIG. 12 illustrates the concentration of norethindrone acetate permeated ($\mu$g/cm$^2$) vs. time (h), obtained in in vitro experiments carried out with transdermal patches, which adhesive matrices have the compositions described in Example 4 Δ (OA/LA) and in Example 7 □ (OA), see table XVI.

Figure 13:
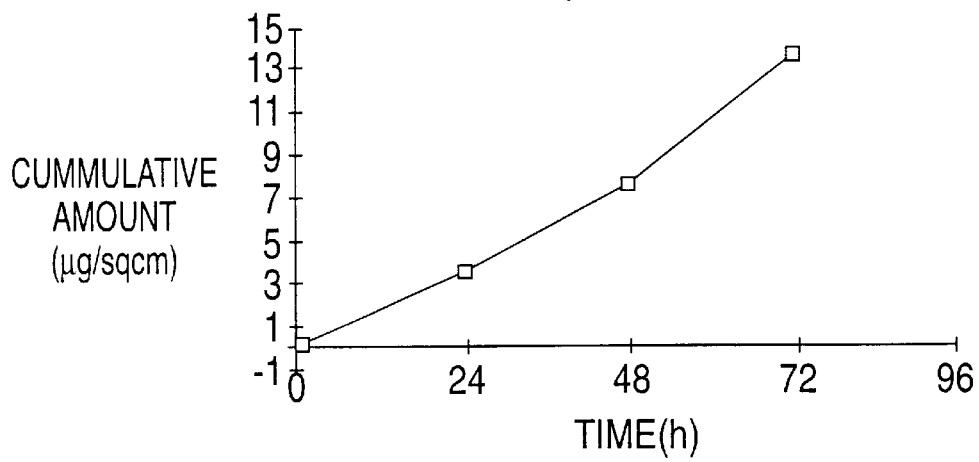
Figure 13:
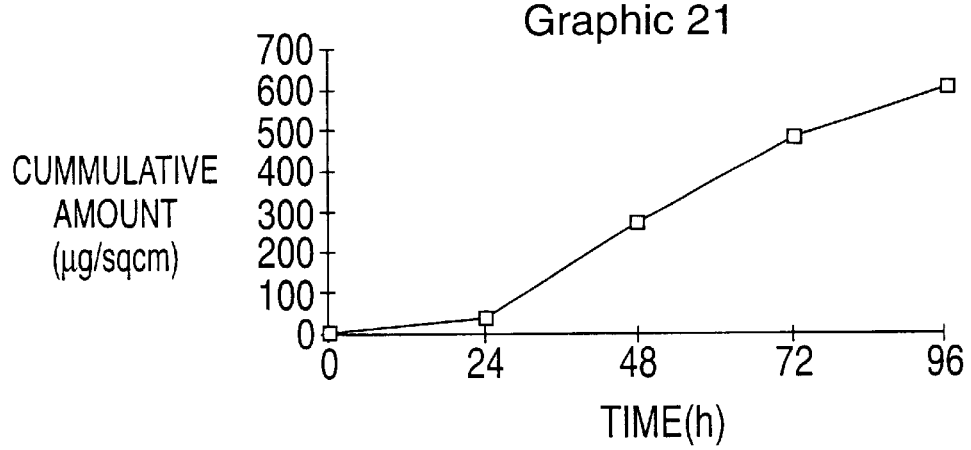
Figure 13:
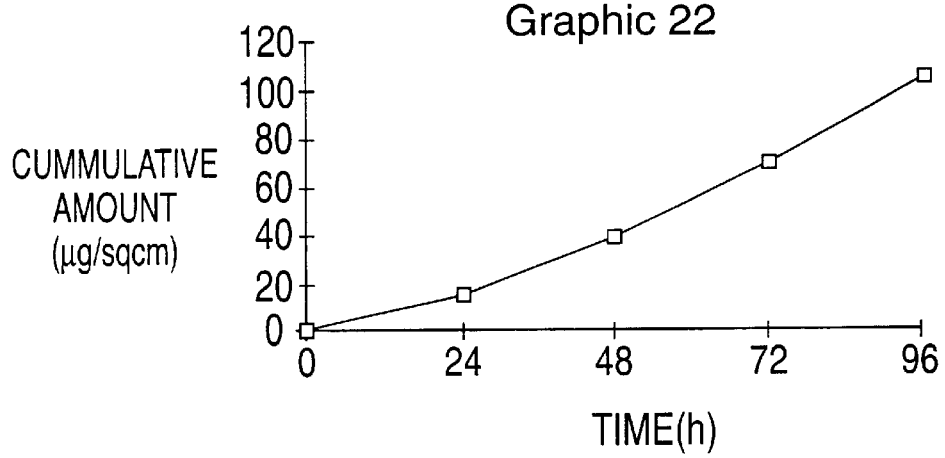

Graphic 20 of FIG. 13 illustrates the permeated drug cumulative amount of Levonorgestrel ($\mu$g/cm$^2$) vs. time (h), wherein the used adhesive matrix is described in Example 35 □ (OA/LA), see table XVII.

Graphic 21 of FIG. 13 illustrates the permeated drug cumulative amount of Alprazolam ($\mu$g/cm$^2$) vs. time (h), wherein the used adhesive matrix is described in Example 36 □ (OA/LA), see table XVII.

Graphic 22 of FIG. 13 illustrates the permeated drug cumulative amount of Testosterone ($\mu$g/cm$^2$) vs. time (h), wherein the used adhesive matrix is described in Example 37 □ (OA/LA), see table XVII.

Figure 14:
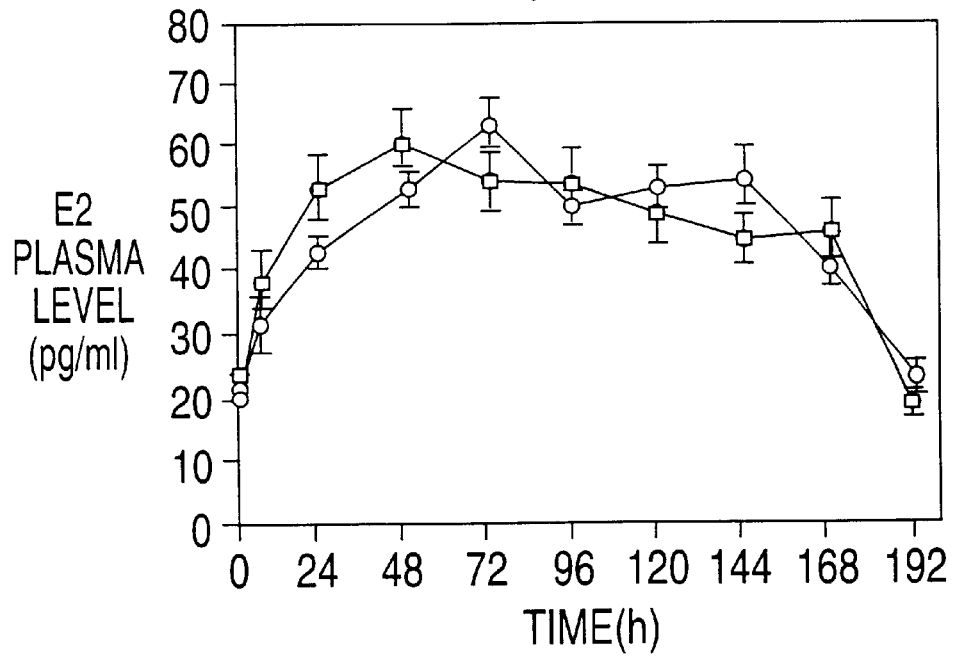
Figure 14:
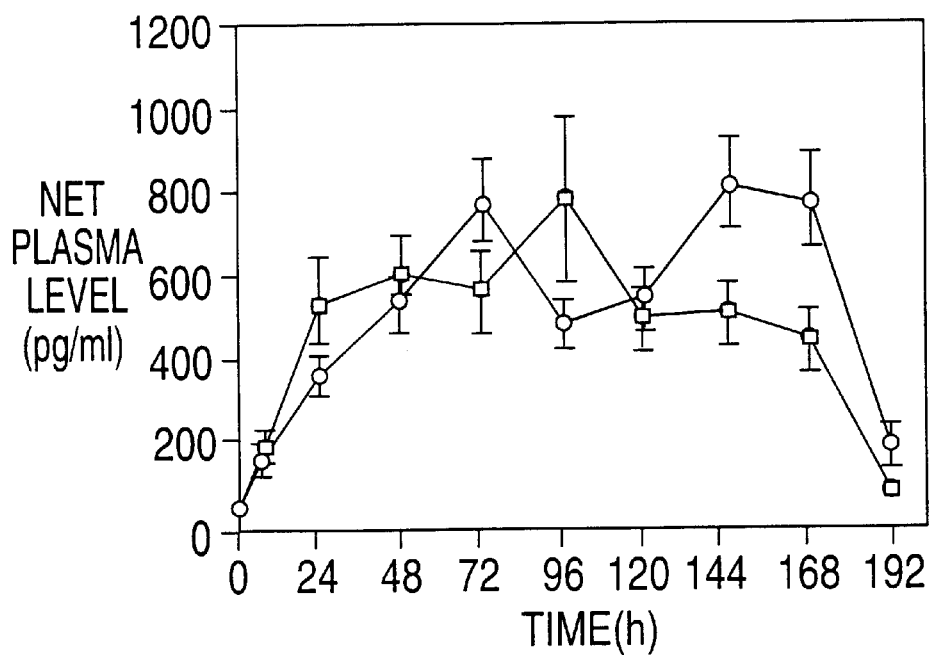

Graphic 23 of FIG. 14 illustrates the serum levels of estradiol, wherein the curve of the combipatch according to the invention is ■ and that of Estragest TTS® according to the prior art is Δ (see table XX).

Graphic 24 of FIG. 14 illustrates the serum levels of norethindrone, wherein the curve of the combipatch according to the invention is ■ and that of Estragest TTS® according to the prior art is Δ (see table XXI).

DETAILED DESCRIPTION OF THE INVENTION

An objective of this invention is to provide a formulation which shows adequate transdermal penetration enhancement effect for many active agents.

The main objective of this invention is to provide a patch formulation which offers adequate and sustained transdermal penetration enhancement for many active agents, or a mixture thereof.

Accordingly, it is an object of the present invention to provide a skin permeation enhancer composition comprising of a first component that is a saturated fatty acid or alcohol given by the formula $CH_3$—$(CH_2)_n$—$COOH$ or $CH_3$—$(CH_2)_n$—$CH_2OH$ respectively, in which n is an integer from 6 to 16, preferably 8 to 12, most preferably 10; and a second component that is a monounsaturated fatty acid or alcohol given by the formula $CH_3$—$(C_nH_{2(n-1)})$—$COOH$ or $CH_3$—$(C_nH_{2(n-1)})$—$CH_2OH$ respectively, in which n is an integer from 8 to 22, preferably 14 to 18, most preferably 16, in an adhesive matrix, preferably acrylic type, a tackifier agent, preferably pentaerithritol ester of saturated abietic acid, and a cohesive improver, preferably ethylcellulose. The monolithic matrix layer may also comprise additional components such as diluents, solubilizers, stabilizers, vehicles, biocides, antioxidants, anti-irritants and the like.

A transdermal delivery system according to the invention comprises one or more active agents, or mixture thereof.

The transdermal delivery system of this invention comprises:

a) a backing layer which is substantially impervious to drugs to be delivered transdermally and which optionally is breathable, especially if the device is used on a long term basis, such as for several days.

b) an adhesive polymeric matrix which is in contact with said backing layer and which has dissolved and/or microdispersed therein an effective amount of a drug or a combination of two or more drugs; said polymer layer provides a dosage amount of the drugs to be delivered transdermally; said adhesive layer adheres the transdermal device in intimate contact with the skin of the subject being treated to permit the drugs to be absorbed transdermally; said adhesive layer contains an effective amount of a suitable permeation enhancer combination, integrated by one or more fatty acids and/or one or more fatty alcohols.

c) a protective release liner, which is removed at the time of use. The term "drug" as used to describe the principal active ingredient of the device intends a biologically active compound or mixture compounds that has a therapeutic, prophylactic or other beneficial pharmacological and/or physiological effect on the user of the device. Examples of types of drugs that may be used in the inventive device are antiinflammatory drugs, analgesics, antiarthritic drugs, tranquillizers, narcotic antagonists, antiparkinsonian agents, anticancer drugs, immunosupression agents, antiviral agents, antibiotic agents, appetite suppressants, antiemetics, anticholinergics, antihistaminics, antimigraine agents, coronary, cerebral or peripheral vasodilators, antianginals, e.g., calcium channel blockers, hormones, contraceptive agents, antithrombotic agents, diuretics, antihypertensive agents, cardiovascular drugs, chemical dependency drugs, alpha adrenergic blocking agents (alpha blocker) and the like. The appropriate drugs of such types are capable of permeating through the skin either inherently or by virtue of the effect onto the skin with our enhancer composition. Because the size of the device is limited for patient acceptance reasons, the preferred drugs are those which are effective at low concentration in the blood stream. Examples of specific drugs are steroids such as estradiol, progesterone, norethindrone, norethindrone acetate, levonorgestrel, ethynodiol diacetate, norgestamate, gestodene, desogestrel, 3-keto desogestrel, demegestone, promegestone, normergestrel, testosterone, dehydroepiandrosterone, hydrocortisone, and their esters; nitro compounds such as amyl nitrate, nitroglycerin and isosorbide nitrates; amine compounds such as nicotine, chlorpheniramine, terfenadine and triprolidine, oxicam derivatives such as piroxicam; anti-inflammatory, antipyretic or analgesics such as indomethacin, diclofenac, ketoprofen, ketorolac; mucopolysacharidases such as thiomucase; opioids such as buprenorphine, fentanyl, and fentanyl derivatives or analogs, naloxone, codeine, dihydroergotamine, pizotiline, salbutamol and terbutaline; prostaglandins such as those in the PGA, PGB, PGE series, e.g. alprostadil and PGF series, e.g., misoprostol and emprostil, omeprazole; benzamides such as metoclopramide and scopolamine; peptides such as growth hormon releasing factor, growth factors (EGF, TGF, PDGF and the like), and somastostatin; clonidine; dihydropyridines such as nifedipine, verapamil, diltiazem, ephedrine, propranolol, metoprolol and spironolactone; thiazides such as hydrochlorotiazide and flunarizine; sydononimines such as molsidomine; sulfated polysaccharides such as heparin fractions; alpha blockers selective for the alpha sub 1 receptor subtype such as alfuzosin, tamsulosin, prazosin and terazosin, short and intermediate half-life benzodiazepine such as alprazolam, bromazepam, lorazepam, oxazepam, temazepam and triazolam, azaspyrodecanediones such as buspirone, butyrophenones such as haloperidol, dihydropyridines such as amlodipine, aporfines such as apomorphine, ergolines such as bromocriptine, pergolide, propinilamines such as selegiline, cyclohexylmandelates such as oxybutynin and the salts of such compounds with pharmaceutically acceptable acids or bases, as the case may be. It can be understood herein that the active agent is intended to mean a single active agent or a combination of more than one active agent.

A backing layer prevents passage of the active agent through the surface of the reservoir distal to the skin, and provides support for the system. The backing layer is made from materials that are substantially impermeable with regard to the drugs of the transdermal dosage unit. It can be made of polymers such as polyethylene, polypropylene, polyurethane, polyvinylchloride, polyesters such as poly (ethylene phthalate), and foils such as laminates of polymer films with metallic foils such as aluminium foil. If the dosage units are used on long term basis, such as for a multiple of days. Examples are Scotchpak products 1012, 1220, 1006, 9722, 9729, etc., from 3M.

A release liner can be included in the transdermal delivery device as manufactured, as it is well known in the art. The release liner is removed before the application of the transdermal delivery device to the skin. Suitable release liners are polyethylene or polyester films coated with a silicone layer, such as Daubert HDPE 164Z, Daubert PESTR 164 Z, Release International 5-EST-A-S242M, Adhesives Research Inc. ML 7138 and ML 8329, Rexam Release FL 2000 Liners, 15989,S 5MIL CL PET 92A/000, 10668 5MIL CL PET A10/000, etc.

The adhesive polymer can preferably be made of a suitable polymeric adhesive, such as a suitable copolymer of acrylic acid esters with vinylacetate, cross-linked or not cross-linked or a silicone adhesive or a suitable polyisobutylene. Examples of acrylic polymers are Duro Tak 2153, 2852, 2516, 2287 and 2620, etc. from National Starch and Chemical Co; and Gelva MAS 737, and 788 etc. from Monsanto Co; Dow Corning silicone adhesives 97-9179 and 97-9120. etc.; Vistanex PIB adhesive series manufactured by Exxon, etc.

The tackifier agent is preferably a suitable resin or rosin that provides adequate tack properties to the adhesive formulation, such as pentaerythritol esters of highly hydrogenated rosin, e.g. Foral 105-E; glycerol esters of highly hydrogenated rosin, e.g. Foral 85-E; pentaerythritol esters of partially hydrogenated rosin, e.g. Foralyn 110, Pentatyn H-E; pentaerythritol esters of rosin, e.g. Pentatyn A, Permalyn 5110, 6110, 5135; glycerol esters of hydrogenated rosin, e.g. Foralyn 90; Staybelite ester 10-E; triethylene glycol esters of hydrogenated rosin, e.g. Staybelite ester 3, from Hercules Inc. etc.

Some cohesive improvers may be added, which are effective improving the cohesive properties of the adhesive formulation, e.g. cellulose derivatives, such as ethylcellulose (Ethocel), EHEC, HPMC (Methocel) nitrocellulose, cellulose acetate, CMC, HPC (Klucel); natural gums such as arabic, xanthan, guar gums, etc.; acrylic acid polymers, partially cross-linked with polyfunctional allyl-esthers, containing 56%–68% of free —COOH groups, of the type "Carbomer" such as "carbopol 934, 974, 980, ETD 2020, ETD 2001, Ultrez 10", etc.; copolymers of methacrylic acid alkyl-esters wherein some alkyl groups contain quaternarized amino groups such as Eudragit E-100, RL, RS, NE 30D, etc.; polyvinylpyrrolidone derivatives such as Kollidon CL, VA 64, etc.; polyoxyethylene polyoxypropylene copolymer such as Lutrol F grades 127, 68, etc.

Carriers and/or vehicles suitable for transdermal administration include liquid, solvent, solubilizer, or the like e.g. polyhidricalcohols such as glycerol, propylene glycol, polyethylene glycol, hexylene glycol, ethyl acetate, ethyl alcohol, isopropyl alcohol, etc.

Antioxidants and/or preservatives suitable for transdermal administration such as butyl hydroxy toluene (BHT), butyl hydroxy anisole (BHA), DL-alfa tocoferol, antioxidant complex, edetate, edetate disodium, etc.

The adhesive layer is desirably thin in the micron-range thickness, suitably 25–250 microns, desirably 40–200 microns, and preferably about 50–150 microns in thickness.

The saturated and unsaturated fatty acids and/or the fatty alcohols that act as permeation enhancers are incorporated thoroughly in the adhesive polymer. Specific skin permeation enhancers which can be used to make the monolithic transdermal device of this invention include saturated and unsaturated fatty acids and alcohols, such as oleic acid, oleyl alcohol, stearic acid, stearyl alcohol, palmitic acid, palmityl alcohol, myristyl alcohol, myristic acid, lauric acid, lauryl alcohol, capric acid, decyl alcohol, etc.

The preferred embodiment is basically a monolithic transdermal system having the following composition by weight: 20–85% adhesive polymer, 5–25% tackifier agent, 0.5–15% active agent(s), 3–18% of a fatty acid or a fatty alcohol and 3–18% of other fatty acid or other fatty alcohol with different chain lengths.

The transdermal therapeutic systems of this invention may be fabricated by state of the art methods such as melt blending, solution, coating, drying, film lamination and die cutting following by the packaging process, as it is disclosed by Dohner in "Transdermal Controlled Systemic Medications", Marcel Dekker, New York 1987, pages 349–364.

Although the mechanism of the enhancer combination herein discloses is not fully clear by the scientific knowledge up to now, it can be explained as follows:

It is possible that fatty acids or fatty alcohols are mainly distributed to the stratum corneum because of its lipophilicity, and interact with the stratum corneum lipids ("pull"). And the fatty acids or fatty alcohols that remain within the matrix increase the thermodynamic activity of the active agent within the monolithic matrix ("push").

It is likely that fatty acids or fatty alcohols that have the tendency to remain within the adhesive matrix, elicit a promotion in the release of the other fatty acids or alcohols and to the drug. This effect could thus result in a more rapid and sustained diffusion of the active agent molecules across the skin.

Moreover, if the "pull" effect is the responsible for the enhancement, it is likely that lauric acid or lauryl alcohol exerts higher enhancement factor in the early times, while the oleic acid or oleyl alcohol enhances the permeation rates of the drug in the later times. Moreover, a mixture of the above mentioned penetration enhancers conduct us to provide adequate and sustained drug serum levels throughout 7 days.

This invention relates to a novel composition for transdermal application to humans and methods for providing therefrom a controlled dosage of active agent(s).

Use of combination of two or more skin penetration enhancer compounds, with different physico-chemical properties or different chemical family, frequently result in superior effects, such as improved transdermal absorption, but it is presently herein that the combination of penetration enhancers of the same chemical family, resulted in controlled and sustained percutaneous absorption of the drugs throughout a 7 day period.

In the preferred embodiment of the present invention, the active agent(s) is dissolved in said transdermal formulation in amount comprised from 0.5 to 15.0%. One fatty acid selected, lauric acid, is comprised from 3.0 to 18.0% (w/w), preferably 4.0 to 15.0% (w/w) and most preferably 12.0% (w/w) and the second fatty acid selected, oleic acid is comprised from 3.0 to 18.0% (w/w), preferably 5.0 to 15.0% (w/w) and most preferably 6.0% (w/w). A tackifier agent, Foral 105-E, comprises from 5.0 to 25.0% (w/w), preferably 7.0 to 15.0% (w/w) and most preferably 10.0% (w/w). Ethylcellulose, is used for improving and balancing the adhesive properties (adhesion and cohesion) is comprised from 0.1 to 5.0% (w/w), preferably 0.1 to 1.5% (w/w), and most preferably 0.3% (w/w). BHT and BHA as antioxidants are comprised from 0.01 to 1.5% (w/w),preferably 0.01 to 0.8% (w/w), and most preferably 0.03% (w/w) for BHA. and 0.3% (w/w) for BHT. And finally the acrylic adhesive polymer Duro Tak 87-2852 a moderate molecular weight, self cross-linking, acrylic co-polymer pressure sensitive adhesive supplied in an organic solvent which contains ethyl acetate (65%w/w); isopropanol (19%w/w); hexane (12%w/w); toluene (2%w/w) comprises from 20.0 to 85.0% (w/w), preferably 40.0 to 80.0% (w/w) and most preferably 62.0% (w/w).

The percentage is being based on the total weight of the said dosage form.

Modifications can be suggested to those skilled in the art to the chemical structures represented by oleic acid and lauric acid, which do not detract substantially from their function as preferred permeation enhancers.

It will be suggested to those skilled in the art to use other drugs or fatty acids or fatty alcohols, in forming the dosage units of this invention. Such use of others drug or fatty acids or fatty alcohols are intended to be within the scope of this invention insofar.

Definition of Terms

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers, and in particular, through the use of the enhancer composition of the present invention, can be observed by measuring the rate of diffusion of drug through animal or human skin using a diffusion cell apparatus as described in the examples herein.

An "effective" or an "adequate" permeation enhancer as used herein means a permeation enhancer that will provide the desired increase in skin permeability and correspondingly, the desired depth of penetration, rate of administration, and amount of drug delivered.

By "transdermal" delivery, applicants intend to include both transdermal (or "percutaneous") and transmucosal administration, i.e., delivery by passage of a drug through the skin or mucosal tissue and into the bloodstream.

By "monolithic system", as used herein describes a transdermal drug delivery system, in which the drug is dissolved or dispersed in a matrix, which becomes the drug reservoir and contains also the pressure sensitive adhesive which assures the adhesion of the transdermal devices to the skin. In these systems the release of the active agent from the matrix takes place by diffusion.

By "tackifier agents" refer to resin suitable for transdermal drug administration that will provide the increase in the tack properties of the adhesive. Such materials are typically natural occurring resinous or rosinous materials or truly synthetic polymer materials, such as glycerol or pentaeritritol ester of abietic acid, etc.

By "cohesive improver" is meant any material or polymer suitable, which is effective in the improvement of the cohesive strength of adhesive formulation or composition, such as cellulose derivatives, carbomer, polymethacrylates, etc.

"Carriers" or "vehicles" as used herein refer to carrier materials suitable for transdermal drug administration, and include any such materials known in the art, e.g., any liquid, solvent, liquid diluent, solubilizer, or the like, which is non-toxic and which does not interact with other components of the composition in a deleterious manner. Examples of suitable vehicles for use herein include water, alcohols, polyalcohols, glycols, ethyl acetate, etc.

By the term "pharmacologically active agent" or "drug" as used herein is meant any chemical material or compound suitable for transdermal or transmucosal administration which induces a desired systemic effect.

By the term "fatty acid or fatty alcohol" is meant any saturated fatty acid or alcohol having from 8 to 18 carbon atoms or any unsaturated fatty acid or fatty alcohol having from 8 to 24 carbon atoms which is effective in enhancing the penetration of drug through the mammalian skin. In addition, any combination of fatty acids and fatty alcohols having the above specified number of carbon atoms which is effective in enhancing transdermal drug penetration may be used. Preferred permeation enhancer fatty acids or fatty alcohols are those with 12–18 carbon atoms or any mixture thereof. Especially preferred penetration enhancing fatty acids and fatty alcohols are those with 12 carbon atoms, such as lauric acid and lauryl alcohol and with 18 carbons such as oleic acid and oleyl alcohol. It should be understood that the terms "penetration enhancer", "permeation enhancer" and "fatty acid or fatty alcohol" will be used interchangeably throughout the remainder of the specification.

By "therapeutically effective" amount of a pharmacologically active agent is meant a non-toxic but sufficient amount of a compound to provide the desired therapeutic effect.

By the term "controlled and sustained release" is designated a gradual release at a predetermined time and at a desired rate during a predetermined release period.

The examples described herein have a design in which the drug is included into the pressure sensitive adhesive polymer. The adhesive layer is protected on one side by an impermeable film (backing), and on the other side by a siliconised removable release liner.

The device preparation was made in the laboratory using a Mathis Labcoater and Mathis Labdryer equipment by a direct coating process in which the adhesive matrix is applied onto the release liner, then the solvent was evaporated off, and then the backing sheet was applied onto the adhesive film by way of a lamination procedure.

The coating process was made as described below:

A fixed Doctor knife is mounted across the entire width of the carrier material, and the polymer is extended in front of the knife, which spreads a layer onto the release liner running beneath. The thickness of the layer is determined primarily by the distance of the knife from the release liner. The release liner runs inside a drier chamber in which the adhesive matrix is solidified by evaporating off the solvents carrying out a gradually increasing of the temperature and fan speed as showed below:

| Drying step | Time (min.) | Temperature (° C.) | Fan speed (rpm) |
| --- | --- | --- | --- |
| 1 | 15 | 40 | 700 |
| 2 | 20 | 55 | 1000 |
| 3 | 25 | 70 | 1200 |

The described sequence permits the elimination of the solvents avoiding its occlusion by superficial drying.

After drying, the lamination process is performed, in this step the backing sheet is applied onto the adhesive layer, obtaining an adhesive matrix thickness between 80 and 100 $\mu$m.

Finally the sheet is die cut in circles with an area of 2.54 cm$^2$ in order to obtain an appropriate size for the studies.

The coating and lamination methods are well described in the literature: Satas D., 1989; Grant O. W. and Satas D., 1984; Mushel L. A., 1984.

EXAMPLES

The following examples are an illustration of the invention and are not intended to be limiting.

Example 1(PlaceboNEp35)

An adhesive matrix composed by Lauric acid 5.971% (w/w), Oleic acid 6.097% (w/w), Ethylcellulose 0.253% (w/w), Foral 105-E (tackifier) 9.929% (w/w), Duro Tak 87-2852 (37.1% solution) 77.717% (w/w), BHT 0.030% (w/w), BHA 0.003% (w/w), was prepared according to the manufacturing technique herein described.

Example 2(PlaceboNEp36)

An adhesive matrix composed by Lauric acid 5.995% (w/w), Ethylcellulose 0.253% (w/w), Foral 105-E 9.922% (w/w), Duro Tak 87-2852 (37.1% solution) 83.797% (w/w), BHT 0.030% (w/w), BHA 0.004% (w/w), was prepared according to the manufacturing technique herein described.

Example 3(PlaceboNEp37)

An adhesive matrix composed by Oleic acid 6.017% (w/w), Ethylcellulose 0.256% (w/w), Foral 105-E 9.978% (w/w), Duro Tak 87-2852 (37.1% solution) 83.716% (w/w), BHT 0.029% (w/w), BHA 0.004% (w/w), was prepared according to the manufacturing technique herein described.

Example 4(Nep136)

An adhesive matrix composed by Norethindrone Acetate 7.510% (w/w), 17$\beta$-Estradiol 1.507% (w/w), Lauric acid 12.004% (w/w), Oleic acid 6.115% (w/w), Ethylcellulose 0.245% (w/w), Foral 105-E 10.048% (w/w), Duro Tak 87-2852 (35.9% solution) 62.537% (w/w), BHT 0.030% (w/w), BHA 0.003% (w/w), was prepared according to the manufacturing technique herein described

Example 5(Nep140)

An adhesive matrix composed by Norethindrone Acetate 7.531% (w/w), 17$\beta$-Estradiol 1.495% (w/w), Glycerol Mono Oleate 6.091% (w/w), Ethylcellulose 0.250% (w/w), Foral 105-E 9.974% (w/w), Duro Tak 87-2852 (37.6% solution) 74.630% (w/w), BHT 0.026% (w/w), BHA 0.003% (w/w), was prepared according to the manufacturing technique herein described

Example 6(Nep141)

An adhesive matrix composed by Norethindrone Acetate 7.530% (w/w), 17$\beta$-Estradiol 1.500% (w/w), Glycerol Mono Laurate 6.015% (w/w), Ethylcellulose 0.247% (w/w), Foral 105-E 9.983% (w/w), Duro Tak 87-2852 (37.6% solution) 74.695% (w/w), BHT 0.026% (w/w), BHA 0.004% (w/w), was prepared according to the manufacturing technique herein described

Example 7(Nep135)

An adhesive matrix composed by Norethindrone Acetate 7.490% (w/w), 17$\beta$-Estradiol 1.506% (w/w), Oleic acid 5.965% (w/w), Ethylcellulose 0.262% (w/w), Foral 105-E 9.973% (w/w), Duro Tak 87-2852 (35.9% solution) 74.767% (w/w), BHT 0.033% (w/w), BHA 0.003% (w/w), was prepared according to the manufacturing technique herein described

Example 8(Nep142)

An adhesive matrix composed by Norethindrone Acetate 7.513% (w/w), 17$\beta$-Estradiol 1.508% (w/w), Isopropyl Myristate 6.088% (w/w), Ethylcellulose 0.275% (w/w), Foral 105-E 10.017% (w/w), Duro Tak 87-2852 (37.6% solution) 74.563% (w/w), BHT 0.033% (w/w), BHA 0.004% (w/w), was prepared according to the manufacturing technique herein described

Example 9(Nep143)

An adhesive matrix composed by Norethindrone Acetate 7.493% (w/w), 17$\beta$-Estradiol 1.529% (w/w), Glyceryl mono di Caprylate 6.022% (w/w), Ethylcellulose 0.247% (w/w), Foral 105-E 10.028% (w/w), Duro Tak 87-2852 (37.6% solution) 74.650 % (w/w), BHT 0.029% (w/w), BHA 0.003% (w/w), was prepared according to the manufacturing technique herein described

Example 10(Nep123)

An adhesive matrix composed by Norethindrone Acetate 7.475% (w/w), 17$\beta$-Estradiol 1.494% (w/w), Ethylcellulose 0.244% (w/w), Foral 105-E 10.000% (w/w), Duro Tak 87-2852 (37.7% solution) 80.758% (w/w), BHT 0.027% (w/w), BHA 0.003% (w/w), was prepared according to the manufacturing technique herein described.

Example 11(Alp010)

An adhesive matrix composed by Alprazolam 7.356% (w/w), Ethylcellulose 0.486% (w/w), Foral 105-E 9.801% (w/w), Duro Tak 87-2852 (37.2% solution) 82.325% (w/w), BHT 0.027% (w/w), BHA 0.006% (w/w), was prepared according to the manufacturing technique herein described.

Example 12(Alp012)

An adhesive matrix composed by Alprazolam 7.364% (w/w), Oleic Acid 5.846% (w/w), Ethylcellulose 0.491% (w/w), Foral 105-E 9.809% (w/w), Duro Tak 87-2852 (37.2% solution) 76.454% (w/w), BHT 0.030% (w/w), BHA 0.005% (w/w), was prepared according to the manufacturing technique herein described

Example 13(Alp013)

An adhesive matrix composed by Alprazolam 7.290% (w/w), Oleic Acid 5.853% (w/w), Lauric Acid 5.829% (w/w), Ethylcellulose 0.481% (w/w), Foral 105-E 9.717% (w/w), Duro Tak 87-2852 (37.2% solution) 70.794% (w/w), BHT 0.029% (w/w), BHA 0.006% (w/w), was prepared according to the manufacturing technique herein described

Example 14(TTp001)

An adhesive matrix composed by Testosterone 2.755% (w/w), Oleic Acid 5.638% (w/w), Lauric Acid 11.022% (w/w), Ethylcellulose 0.226% (w/w), Foral 105-E 9.108% (w/w), Duro Tak 87-2852 (36.0% solution) 71.219% (w/w), BHT 0.028% (w/w), BHA 0.004% (w/w), was prepared according to the manufacturing technique herein described

Example 15(TTp002)

An adhesive matrix composed by Testosterone 3.009% (w/w), Ethylcellulose 0.264% (w/w), Foral 105-E 9.995% (w/w), Duro Tak 87-2852 (36.0% solution) 86.697% (w/w), BHT 0.032% (w/w), BHA 0.003% (w/w), was prepared according to the manufacturing technique herein described

Example 16(TTp005)

An adhesive matrix composed by Testosterone 2.296% (w/w), Ethylcellulose 0.250 % (w/w), Foral 105-E 9.895% (w/w), Oleic Acid 6.053% (w/w), Duro Tak 87-2852 (35.9% solution) 80.808% (w/w), BHT 0.025% (w/w), BHA 0.006% (w/w), was prepared according to the manufacturing technique herein described

Example 17(Nep144)

An adhesive matrix composed by Norethindrone Acetate 7.527% (w/w), 17β-Estradiol 1.504% (w/w), Lauric acid 11.991% (w/w), Oleyl alcohol 6.090% (w/w), Ethylcellulose 0.247% (w/w), Foral 105-E 10.035% (w/w), Duro Tak 87-2852 (36.0% solution) 62.572% (w/w), BHT 0.031% (w/w), BHA 0.003% (w/w), was prepared according to the manufacturing technique herein described

Example 18(Nep145)

An adhesive matrix composed by Norethindrone Acetate 7.516% (w/w), 17β-Estradiol 1.499% (w/w), Lauryl alcohol 12.160% (w/w), Oleyl alcohol 6.067% (w/w), Ethylcellulose 0.254% (w/w), Foral 105-E 10.011% (w/w), Duro Tak 87-2852 (36.0% solution) 62.459% (w/w), BHT 0.030% (w/w), BHA 0.005% (w/w), was prepared according to the manufacturing technique herein described

Example 19(Nep137)

An adhesive matrix composed by Norethindrone Acetate 7.321% (w/w), 17β-Estradiol 1.464% (w/w), Lauric acid 11.712% (w/w), Oleic acid 5.949% (w/w), Ethylcellulose 0.251% (w/w), Foral 105-E 19.517% (w/w), Duro Tak 87-2852 (37.6% solution) 53.754% (w/w), BHT 0.030% (w/w), BHA 0.003% (w/w), was prepared according to the manufacturing technique herein described

Example 20(Np003)

An adhesive matrix composed by Norethindrone Acetate 7.305% (w/w), Ethylcellulose 0.250% (w/w), Foral 105-E 9.666% (w/w), Duro Tak 87-2852 (36.2% solution) 82.751% (w/w), BHT 0.027% (w/w), BHA 0.001% (w/w), was prepared according to the manufacturing technique herein described

Example 21 (Np004)

An adhesive matrix composed by Norethindrone Acetate 7.517% (w/w), Oleyl alcohol 6.094% (w/w), Ethylcellulose 0.259% (w/w), Foral 105-E 9.929% (w/w), Duro Tak 87-2852 (36.2% solution) 76.162% (w/w), BHT 0.034% (w/w), BHA 0.006% (w/w), was prepared according to the manufacturing technique herein described

Example 22(Np005)

An adhesive matrix composed by Norethindrone Acetate 7.481% (w/w), Oleyl alcohol 6.112% (w/w),Lauric Acid 11.919% (w/w), Ethylcellulose 0.259% (w/w), Foral 105-E 9.943% (w/w), Duro Tak 87-2852 (36.2% solution) 64.255% (w/w), BHT 0.026% (w/w), BHA 0.005% (w/w), was prepared according to the manufacturing technique herein described

Example 23(Pbo. 03 wt)

An adhesive matrix composed by Oleic Acid 12.18% (w/w),Lauric Acid 12.10% (w/w), Foral 105-E 12.07% (w/w), Duro Tak 87-2852 (36.01% solution) 63.62% (w/w), BHT 0.03% (w/w), BHA 0.005% (w/w), was prepared according to the manufacturing technique herein described

Example 24(Pbo. 16wt)

An adhesive matrix composed by Oleic Acid 12.06% (w/w),Lauric Acid 11.98% (w/w), Ethylcellulose 0.50% (w/w), Foral 105-E 11.98% (w/w), Duro Tak 87-2852 (35.39% solution) 63.45% (w/w), BHT 0.03% (w/w), BHA 0.004% (w/w), was prepared according to the manufacturing technique herein described

Example 25(Pbo. 17 wt)

An adhesive matrix composed by Oleic Acid 11.97% (w/w),Lauric Acid 11.90% (w/w), Ethylcellulose 2.49% (w/w), Foral 105-E 11.89% (w/w), Duro Tak 87-2852 (35.59% solution) 61.72% (w/w), BHT 0.03% (w/w), BHA 0.003% (w/w), was prepared according to the manufacturing technique herein described

Example 26(Pbo. 12 wt)

An adhesive matrix composed by Oleic Acid 12.11% (w/w),Lauric Acid 11.94% (w/w), Ethylcellulose 9.95% (w/w), Foral 105-E 11.96% (w/w), Duro Tak 87-2852 (36.39% solution) 54.00% (w/w), BHT 0.04% (w/w), BHA 0.005% (w/w), was prepared according to the manufacturing technique herein described

Example 27(Pbo. 10wt)

An adhesive matrix composed by Oleic Acid 11.91% (w/w), Lauric Acid 11.89% (w/w), Foral 105-E 23.76% (w/w), Duro Tak 87-2852 (36.39% solution) 52.41% (w/w), BHT 0.03% (w/w), BHA 0.004% (w/w), was prepared according to the manufacturing technique herein described

Example 28(Pbo. 19 wt)

An adhesive matrix composed by Oleic Acid 11.72% (w/w), Lauric Acid 11.61% (w/w), Ethylcellulose 0.48% (w/w), Foral 105-E 23.22% (w/w), Duro Tak 87-2852 (37.23% solution) 52.93% (w/w), BHT 0.03% (w/w), BHA 0.005% (w/w), was prepared according to the manufacturing technique herein described

Example 29(Pbo. 13 wt)

An adhesive matrix composed by Oleic Acid 12.12% (w/w), Lauric Acid 11.95% (w/w), Ethylcellulose 4.98% (w/w), Foral 105-E 23.94% (w/w), Duro Tak 87-2852 (36.39% solution) 46.97% (w/w), BHT 0.03% (w/w), BHA 0.005% (w/w), was prepared according to the manufacturing technique herein described

Example 30(Pbo. 09-02 wt)

An adhesive matrix composed by Oleic Acid 11.76% (w/w), Lauric Acid 11.76% (w/w), Ethylcellulose 9.81% (w/w), Foral 105-E 23.54% (w/w), Duro Tak 87-2852 (37.23% solution) 43.09% (w/w), BHT 0.03% (w/w), BHA 0.005% (w/w), was prepared according to the manufacturing technique herein described

Example 31(Pbo. 11 wt)

An adhesive matrix composed by Oleic Acid 12.82% (w/w), Lauric Acid 11.80% (w/w), Duro Tak 87-2852 (36.39% solution) 75.35% (w/w), BHT 0.03% (w/w), BHA 0.005% (w/w), was prepared according to the manufacturing technique herein described

Example 32(Pbo. 08 wt)

An adhesive matrix composed by Oleic Acid 12.35% (w/w), Lauric Acid 11.86% (w/w), Ethylcellulose 9.89% (w/w), Duro Tak 87-2852 (36.39% solution) 65.86% (w/w), BHT 0.03% (w/w), BHA 0.005% (w/w), was prepared according to the manufacturing technique herein described

Example 33(Nep176)

An adhesive matrix composed by Norethindrone Acetate 7.980% (w/w), 17β-Estradiol 2.190% (w/w), Lauric acid 3.99% (w/w), Oleic acid 9.11% (w/w), Ethylcellulose 0.25% (w/w), Pentalyn A 19.98% (w/w), Duro Tak 87-2852 (37.6% solution) 56.45% (w/w), BHT 0.030% (w/w), BHA 0.006% (w/w), was prepared according to the manufacturing technique herein described

Example 34(Nep205)

An adhesive matrix composed by Norethindrone Acetate 7.990% (w/w), 17β-Estradiol 2.200% (w/w), Lauric acid 3.99% (w/w), Oleyl alcohol 8.98% (w/w), Ethylcellulose 0.25% (w/w), Pentalyn A 19.98% (w/w), Duro Tak 87-2852 (37.6% solution) 56.58% (w/w), BHT 0.030% (w/w), BHA 0.004% (w/w), was prepared according to the manufacturing technique herein described

Example 35(LNEp006)

An adhesive matrix composed by Levonorgestrel 0.807% (w/w), 17β-Estradiol 1.994 % (w/w), Lauric acid 3.99% (w/w), Oleic acid 9.07% (w/w), Ethylcellulose 0.25% (w/w), Pentalyn A 19.93% (w/w), Duro Tak 87-2852 (37.6% solution) 63.93% (w/w), BHT 030% (w/w), BHA 0.004% (w/w), was prepared according to the manufacturing technique herein described

Example 36(Alp006)

An adhesive matrix composed by Alprazolam 7.400% (w/w), Lauric acid 5.940% (w/w), Oleic acid 5.910% (w/w), Ethylcellulose 0.490% (w/w), Foral 105 E 9.770% (w/w), Duro Tak 87-2852 (37.0% solution) 70.450% (w/w), BHT 0.030% (w/w), BHA 0.005% (w/w), was prepared according to the manufacturing technique herein described

Example 37(Ttp036)

An adhesive matrix composed by Testosterone 8.990% (w/w), Lauric acid 3.97% (w/w), Oleic acid 9.09% (w/w), Ethylcellulose 0.50% (w/w), Pentalyn A 9.97% (w/w), PVP K30 9.97% (w/w), Duro Tak 87-2852 (37.0% solution) 57.55% (w/w), BHT 0.030% (w/w), BHA 0.003% (w/w), was prepared according to the manufacturing technique herein described

In Vitro Enhancer Release Studies

The release of lauric acid and oleic acid was analyzed using paddle over disk method (apparatus 5, USP 23, Drug Release 724).

Figure 1:
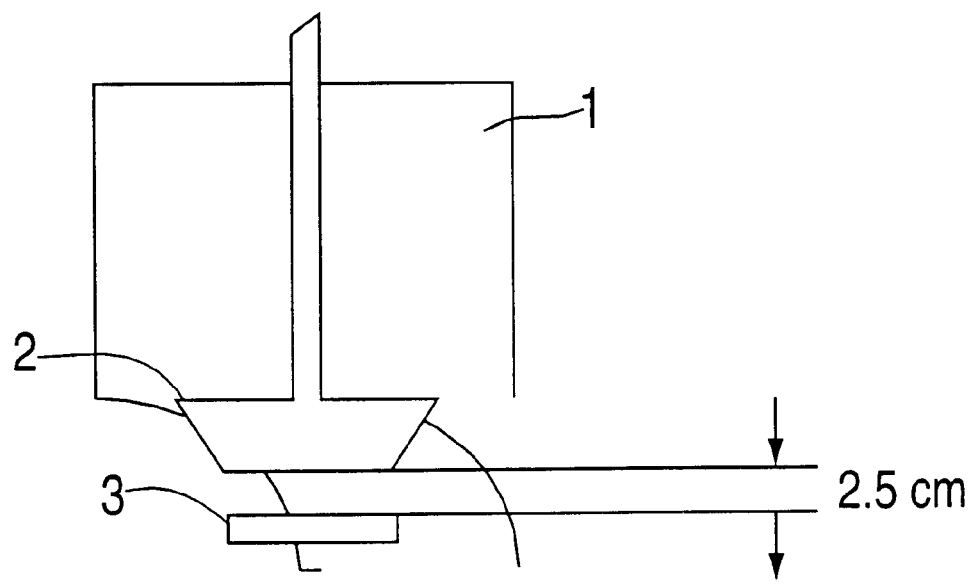

FIG. 1 schematically shown the apparatus mentioned before. In these experiments we have determined the release profiles of lauric acid and oleic acid from transdermal patches, measuring the remaining drug (by means of HPLC techniques) in samples taken at different time points.

The examples used were: Example 1; Example 2 and Example 3.

The dissolution conditions used were: paddle speed: 50 rpm; temperature: 32° C.; dissolution medium: aqueous solution of sodium dodecyl sulphate 0.3%; volume: 500 ml; sample program: 0.5; 1.0; 2.0; 4.0; 8.0 and 24 h.

The results obtained are described in Table I that shows the remaining lauric acid values obtained from Example 1 and Example 2. Table II shows the remaining oleic acid values obtained from Example 1 and Example 3.

TABLE I

| | Remaining Lauric Acid (%) | | | |
| --- | --- | --- | --- | --- |
| Time | Example 1 | | Example 2 | |
| (h) | Mean | SD | Mean | SD |
| 0.5 | 77.23 | 1.93 | 78.72 | 0.10 |
| 1 | 62.42 | 3.49 | 73.34 | 1.32 |
| 2 | 47.92 | 1.48 | 60.10 | 1.42 |
| 4 | 28.65 | 0.16 | 43.07 | 0.94 |
| 8 | 8.67 | 0.92 | 20.52 | 0.82 |
| 24 | 0.53 | 0.08 | 2.68 | 0.34 |

TABLE II

| Time | Remaining Oleic Acid (%) | | | |
|---|---|---|---|---|
| | Example 1 | | Example 3 | |
| (h) | Mean | SD | Mean | SD |
| 0.5 | 93.30 | 2.18 | 96.54 | 4.86 |
| 1 | 88.89 | 3.34 | 90.27 | 1.84 |
| 2 | 87.07 | 6.32 | 81.20 | 11.69 |
| 4 | 80.19 | 1.94 | 79.18 | 0.03 |
| 8 | 60.08 | 0.28 | 64.31 | 2.44 |
| 24 | 19.30 | 0.95 | 29.48 | 0.96 |

In FIG. 3 the graphics represent values from Table I and Table II.

In Graphic 1 are represented the values of remaining penetration enhancers (% by weight) obtained from transdermal patches which adhesive matrix is that in Example 1, containing the combination of lauric acid (indicated in the graphic 1 with ◊) and oleic acid (indicated with Δ), and in Graphic 2 are represented the values of remaining penetration enhancers (% by weight) obtained from Example 2, that contains only lauric acid (indicated in the Graphic 2 with x) and from Example 3, that contains only oleic acid (indicated in the Graphic 2 with ○) as penetration enhancer.

In Vivo Enhancer Release Studies

The delivery of lauric acid and oleic acid to the skin was analyzed in an in vivo study shown below where the in vitro results were corroborated.

The quantity of lauric acid and oleic acid released in vivo to the skin during 96 hours was evaluated, from a transdermal formulation herein described. Six healthy adult volunteers applied the transdermal drug delivery device and after 96 hours of application the patches were removed and the in vivo release profile of the fatty acids were determined by measuring the remaining penetration enhancer (by means of HPLC techniques).

The examples are the same that the used in the in vitro experiment: Example 1, Example 2 and Example 3.

The patches were applied in a dry, normal and intact zone of the abdominal skin, then were removed 96 hs after the application, and placed into flasks properly labeled with the formula and volunteer identification.

In Table III the individual values are showed, mean values and standard deviations of the remaining permeation enhancers (oleic acid and lauric acid) after the removal of the patches, 96 h after application.

TABLE III

| Volunteer identification | Example 1 | | Example 2 | Example 3 |
|---|---|---|---|---|
| | Oleic Acid | Lauric Acid | Lauric Acid | Oleic Acid |
| JR | 97.55% | 73.94% | 83.80% | 105.47% |
| LP | 106.79% | 80.12% | 85.60% | 117.61% |
| DC | 106.79% | 56.37% | 63.40% | 112.15% |
| RK | 95.66% | 50.77% | 58.20% | 106.28% |
| HG | 108.11% | 68.73% | 76.20% | 113.56% |
| GP | 112.64% | 81.47% | 79.20% | 121.05% |
| Mean | 104.59% | 68.56% | 74.40% | 112.69% |
| SD | 6.58% | 12.60% | 11.17% | 6.14% |

In graphics (3,4,5 and 6) of FIGS. 4 and 5 are depicted the individual and mean values of remaining drug shown in Table III.

In such graphics the remaining penetration enhancer (% by weight) is depicted vs. the initials of the subjects undergoing the in vivo experiments and the mean.

In particular, in Graphic 3 and 4 of FIG. 4 are depicted the individual and mean values of remaining oleic acid (% by weight), obtained from transdermal patches, which ahdesive matrices are those described respectively in Example 1 and 3.

In Graphics 5 and 6 of FIG. 5 are depicted the individual and mean values of remaining lauric acid (% by weight), obtained from transdermal patches, which adhesive matrices are those disclosed respectively in Example 1 and 2.

In vitro and in vivo results demonstrate that oleic acid and lauric acid have different releases from an adhesive matrix.

Lauric acid has a rapid release and oleic acid has a slow release. Since both are good penetration enhancers, this difference can be used in the patch design or formulation. The enhancement effect of lauric acid at early times combined to the enhancement effect of oleic acid at late times produces a sustained permeation profile of the drug throughout the application time of the transdermal device.

In Vitro Drug Release Studies

To perform these studies the U.S. Pharmacopeia 23 (1995) paddle over disk method (apparatus of FIG. 1) is used. This apparatus uses basically the dissolution method with the water bath kept at 32±0.5° C. The transdermal patch with release side up glued to a screen of inert material that held at the bottom of the flask by a disk assembly so that the patch is parallel to and 25±5 mm from the bottom of the paddle blade.

The following tables and graphics illustrate the in vitro drug release results:

TABLE IV

| Time | Alprazolam released (%) | | | | | |
|---|---|---|---|---|---|---|
| | Example 11 | | Example 12 (OA) | | Example 13 (OA/LA) | |
| (h) | Mean | SD | Mean | SD | Mean | SD |
| 0.25 | 2.82 | 0.02 | 3.28 | 0.30 | 5.62 | 0.36 |
| 0.5 | 4.28 | 0.04 | 5.12 | 0.22 | 8.84 | 0.64 |
| 1 | 6.24 | 0.18 | 7.37 | 0.09 | 12.95 | 0.81 |
| 1.5 | 7.97 | 0.05 | 9.39 | 0.16 | 16.49 | 1.08 |
| 2 | 10.22 | 0.22 | 11.08 | 0.18 | 18.58 | 0.87 |
| 3 | 12.61 | 0.20 | 13.88 | 0.60 | 23.37 | 0.98 |
| 4 | 13.43 | 0.36 | 16.00 | 0.12 | 28.01 | 1.51 |
| 6 | 16.47 | 0.45 | 19.76 | 0.20 | 34.54 | 2.13 |
| 8 | 19.32 | 0.64 | 23.16 | 0.23 | 40.51 | 2.47 |
| 24 | 33.11 | 1.43 | 40.42 | 0.31 | 67.55 | 2.80 |
| 29 | 38.49 | 1.11 | 45.96 | 0.48 | 76.05 | 2.91 |

OA: Oleic Acid
LA: Lauric Acid

Graphic 7 of FIG. 6 represents the values reported in Table IV.

The concentrations of alprazolam released (%) are reported vs. time (h).

The curve, indicated with Δ, shows the results obtained when the pitch adhesive matrix has the composition disclosed in Example 11; the curve indicated with ○ shows the results obtained from the adhesive matrix described in Example 12 (OA) and the curve indicated with ◊ shows the results obtained from the adhesive matrix in Example 13 (OA/LA).

TABLE V

| | Norethindrone Acetate released (%) | | | | | |
|---|---|---|---|---|---|---|
| Time | Example 4 (OA/LA) | | Example 7 (OA) | | Example 10 | |
| (h) | Mean | SD | Mean | SD | Mean | SD |
| 0.25 | 12.43 | 0.21 | 7.43 | 0.03 | 4.80 | 0.80 |
| 0.5 | 17.18 | 0.37 | 10.08 | 0.01 | 7.17 | 0.71 |
| 1 | 24.87 | 0.34 | 14.56 | 0.02 | 10.90 | 0.57 |
| 1.5 | 31.06 | 0.21 | 18.48 | 0.28 | 14.12 | 0.53 |
| 2 | 34.65 | 0.37 | 21.01 | 0.25 | 16.08 | 0.61 |
| 3 | 42.00 | 0.30 | 25.83 | 0.22 | 19.00 | 0.25 |
| 4 | 47.41 | 0.74 | 29.91 | 0.29 | 21.92 | 3.02 |
| 6 | 55.59 | 1.34 | 36.59 | 0.37 | 29.21 | 0.87 |
| 7.5 | 58.94 | 1.01 | 39.20 | 0.25 | 31.35 | 1.17 |
| 26 | 87.40 | 0.59 | 72.12 | 1.84 | 62.78 | 1.94 |
| 32 | 89.73 | 0.13 | 76.77 | 1.52 | 69.61 | 1.72 |

OA: Oleic Acid
LA: Lauric Acid

Graphic of FIG. 6 represents the values reported in Table V.

The concentrations of norhindrone acetate released (%) are reported vs. time (h).

The □ marked curve shows the results obtained from the patch adhesive matrix composition disclosed in Example 4 (OA/LA).

The curve, marked with ○, shows the results obtained from the patch adhesive matrix having the composition disclosed in Example 7 (OA).

The curve, indicated with Δ shows the results obtained with the adhesive matrix composition of Example 10.

TABLE VI

| | Testosterone Released (%) | | | | | |
|---|---|---|---|---|---|---|
| Time | Example 14 (OA/LA) | | Example 15 | | Example 16 (OA) | |
| (h) | Mean | SD | Mean | SD | Mean | SD |
| 0.25 | 15.70 | 0.96 | 5.45 | 0.70 | 7.59 | 0.32 |
| 0.5 | 25.76 | 1.02 | 9.00 | 0.76 | 12.50 | 0.69 |
| 1 | 33.51 | 0.90 | 11.28 | 0.97 | 16.16 | 0.77 |
| 1.5 | 39.04 | 0.07 | 14.05 | 1.61 | 19.28 | 1.12 |
| 2 | 43.83 | 0.59 | 16.72 | 1.45 | 22.43 | 1.49 |
| 3 | 53.02 | 0.30 | 20.76 | 1.80 | 27.49 | 1.77 |
| 4 | 59.45 | 0.46 | 24.65 | 2.14 | 32.45 | 1.93 |
| 6 | 67.10 | 0.07 | 30.01 | 2.70 | 38.66 | 2.95 |
| 8 | 73.47 | 0.13 | 35.01 | 2.92 | 44.85 | 3.17 |
| 24 | 87.72 | 3.17 | 61.17 | 6.71 | 70.75 | 4.84 |
| 30 | 94.46 | 0.13 | 66.56 | 7.34 | 78.74 | 3.85 |

OA: Oleic Acid
LA: Lauric Acid

Graphic 9 of FIG. 7 represents the values reported in Table VI.

The concentrations of testosterone released (% by weight) are reported vs. time (h).

The curve marked with □ shows the results obtained from the transdermal patch adhesive matrix has the composition disclosed in Example 14 (OA/LA).

The curve marked with Δ shows the results obtained using the adhesive matrix that has the composition disclosed in Example 15.

The ○ curve shows the results obtained with the adhesive matrix of Example 16 (OA).

TABLE VII

| | Norethindrone Acetate released (%) | | | |
|---|---|---|---|---|
| Time | Example 18 (OAL/LAL) | | Example 19 (OA/LA) | |
| (h) | Mean | SD | Mean | SD |
| 0.33 | 15.99 | 1.10 | 11.11 | 0.57 |
| 0.5 | 20.15 | 1.33 | 12.43 | 0.12 |
| 1 | 29.09 | 1.99 | 18.90 | 0.90 |
| 2 | 36.69 | 1.10 | 23.99 | 1.12 |
| 3 | 43.68 | 1.61 | 27.86 | 2.57 |
| 4.66 | 63.36 | 2.63 | 41.56 | 0.30 |
| 6.33 | 72.13 | 3.13 | 46.39 | 1.57 |
| 25 | 98.53 | N.A. | 83.09 | 10.41 |

OA: Oleic Acid
LA: Lauric Acid
OAL: Oleyl Alcohol
LAL: Lauryl Alcohol

Graphic 10 of FIG. 7 represents the values reported in Table VII.

The concentrations of norethyldrone acetate released (%) are reported vs. time (h).

The curve marked with Δ shows the results obtained from the patch adhesive matrix in Example 18 (OAL/LAL).

The □ curve shows the results obtained from the patch adhesive matrix in Example 19 (OA/LA).

TABLE VIII

| | Norethindrone Acetate released (%) | | | | | |
|---|---|---|---|---|---|---|
| Time | Example 20 | | Example 21 (OAL) | | Example 22 (LA/OAL) | |
| (h) | Mean | SD | Mean | SD | Mean | SD |
| 0.25 | 5.20 | 0.02 | 8.30 | 0.34 | 12.82 | 0.25 |
| 0.5 | 7.73 | 0.00 | 12.69 | 0.82 | 18.83 | 0.33 |
| 1 | 11.22 | 0.27 | 18.04 | 0.83 | 27.25 | 0.39 |
| 1.5 | 13.74 | 0.05 | 22.19 | 1.15 | 33.49 | 0.43 |
| 2 | 16.04 | 0.07 | 26.00 | 1.31 | 38.68 | 0.49 |
| 3 | 19.45 | 0.10 | 31.64 | 1.68 | 46.10 | 0.49 |
| 4 | 23.31 | 0.13 | 37.84 | 2.03 | 53.89 | 0.51 |
| 6 | 29.11 | 0.09 | 47.00 | 2.17 | 64.26 | 0.40 |
| 8 | 32.70 | 0.10 | 52.58 | 2.60 | 70.34 | 0.73 |
| 24 | 57.43 | 1.39 | 83.88 | 4.21 | 95.51 | 0.00 |
| 31.5 | 67.69 | 0.29 | 92.94 | 3.50 | 100.19 | 0.11 |

LA: Lauric Acid
OAL: Oleyl Alcohol

Graphic 11 of FIG. 8 represents the values reported in Table VIII.

The concentrations of northindone acetate released (%) are reported vs. time (h).

The curve marked with ◇ shows the results obtained from the patch which adhesive matrix has the composition in Example 20.

The ○ curve shows the results obtained from the adhesive matrix having the composition disclosed in Example 21 (OAL).

The □ curve shows the results obtained from the adhesive matrix of composition as in Example 22 (OAL/LA).

All the in vitro drug release results herein revealed, clearly demonstrated that the use of the invention increase the release of drug(s) from an adhesive polymeric matrix. Consequently an increment in the drug permeation rate is expected.

In Vitro Drug Permeation Studies

Figure 2:
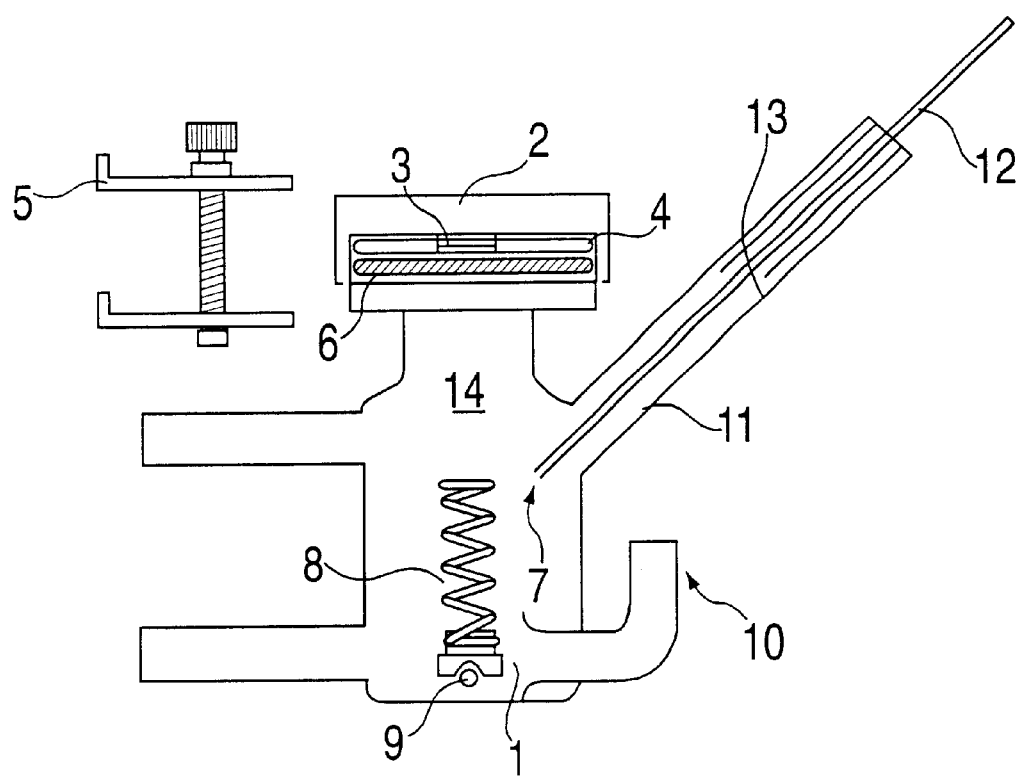

Furthermore, in vitro drug permeation experiments through abdominal guinea pig skin were made using the diffusion chamber that is schematically shown in FIG. 2.

Female guinea pigs, 8 to 16 months of age were shaved on their abdominal skin 72 hs. before sacrificing by cervical dislocation. Only animals that shown absence of lesions were used. A section of full thickness abdominal skin was surgically excised and mounted between the sections of a vertical diffusion cell having 1.77 sqcm of surface area, the epidermal facing up. A given surface of the transdermal devices exemplified previously were applied over the epidermal layer whilst the dermal layer contact with a solution of sodium dodecyl sulfate (SDS), at 35° C. The appearance of the drugs in the inferior compartment (receptor phase) was monitored taking samples at given times and measured afterwards using a high performance liquid chromatography (HPLC) method.

In the in vitro drug permeation studies the examples using the invention herein claimed were compared with examples made using some "well known" permeation enhancers extensively described in the prior art.

The following tables and graphics illustrate the in vitro drug permeation results.

TABLE IX

| | Estradiol Permeated ($\mu$g/sqcm) | | | | | |
|---|---|---|---|---|---|---|
| Time | Example 4 (OA/LA) | | Example 5 (GMO) | | Example 6 (GML) | |
| (h) | Mean | SEM | Mean | SEM | Mean | SEM |
| 0 | 0.00 | 0.00 | 0.00 | 0.00 | 0.00 | 0.00 |
| 24 | 2.26 | 1.14 | 0.00 | 0.00 | 0.42 | 0.42 |
| 48 | 61.70 | 21.26 | 9.90 | 3.86 | 20.79 | 8.76 |
| 72 | 114.73 | 14.11 | 38.13 | 18.73 | 71.03 | 25.23 |
| 96 | 138.16 | 13.36 | 72.5 | 21.15 | 105.28 | 24.76 |

OA: Oleic Acid
LA: Lauric Acid
GMO: Glycerol Mono Oleate
GML: Glycerol Mono Laurate Graphic 12 of FIG. 8 shows the data of Table IX.

The cumulative amount of estradiol permeated ($\mu$g/cm$^2$) is reported vs. time (h).

The curve marked with ● shows the results obtained with the adhesive matrix having the composition in Example 4 (LA/OA).

The ■ curve shows the results obtained from patches which adhesive matrix is that disclosed in Example 5 (GMO).

The curve marked with ▲ shows the results obtained from patches adhesive matrix described in Example 6 (GML).

TABLE X

| | Norethindrone Acetate Permeated ($\mu$g/sqcm) | | | | | |
|---|---|---|---|---|---|---|
| Time | Example 4 (OA/LA) | | Example 5 (GMO) | | Example 6 (GML) | |
| (h) | Mean | SEM | Mean | SEM | Mean | SEM |
| 0 | 0.00 | 0.00 | 0.00 | 0.00 | 0.00 | 0.00 |
| 24 | 11.97 | 6.71 | 1.92 | 0.68 | 2.27 | 0.97 |
| 48 | 340.59 | 105.37 | 47.97 | 27.80 | 106.69 | 48.29 |
| 72 | 653.70 | 77.61 | 196.29 | 113.42 | 376.90 | 145.26 |
| 96 | 797.15 | 73.95 | 373.71 | 127.73 | 597.64 | 150.44 |

OA: Oleic Acid
LA: Lauric Acid
GMO: Glycerol Mono Oleate
GML: Glycerol Mono Laurate Graphic 13 of FIG. 9 shows the data of Table X.

The cumulative amount of northindrone acetate permeated ($\mu$g/cm$^2$) is reported vs. time (h).

The curve marked with ● is obtained from experiments carried out on patches which adhesive matrix has the composition disclosed in Example 4 (OA/LA).

The ■ curve shows the results obtained by using the adhesive matrix disclosed in Example 5 (GMO).

The curve marked with ▲ shows the results obtained by using the adhesive matrix described in Example 8 GML).

TABLE XI

| | Estradiol Permeated ($\mu$g/sqcm) | | | | | |
|---|---|---|---|---|---|---|
| Time | Example 4 (OA/LA) | | Example 8 (IPM) | | Example 9 (GMDC) | |
| (h) | Mean | SEM | Mean | SEM | Mean | SEM |
| 0 | 0.00 | 0.00 | 0.00 | 0.00 | 0.00 | 0.00 |
| 24 | 5.00 | 0.99 | 3.11 | 1.23 | 3.23 | 0.60 |
| 48 | 30.10 | 8.54 | 16.17 | 3.52 | 14.86 | 5.37 |
| 72 | 86.35 | 28.18 | 42.27 | 5.05 | 36.83 | 11.97 |
| 96 | 111.96 | 29.11 | 92.74 | 14.95 | 66.93 | 12.81 |

OA: Oleic Acid
LA: Lauric Acid
IPM: Isopropyl Myristate
GMDC: Glycerol mono di Caprylate Graphic 14 of FIG. 9 represents the values reported in Table XI.

The cumulative amount of estradiol permeated ($\mu$g/cm$^2$) is reported vs. time (h).

The curve indicated with ● shows the results obtained by using the patches which adhesive matrix has the composition as in Example 4 (OA/LA)

The curve indicated with ■ is obtained by using the adhesive matrix disclosed in Example 8 (IPM).

The ▲ curve shows the results obtained from adhesive matrix disclosed in Example 9 (GMDC).

TABLE XII

| | Norethindrone Acetate Permeated ($\mu$g/sqcm) | | | | | |
|---|---|---|---|---|---|---|
| Time | Example 4 (OA/LA) | | Example 8 (IPM) | | Example 9 (GMDC) | |
| (h) | Mean | SEM | Mean | SEM | Mean | SEM |
| 0 | 0.00 | 0.00 | 0.00 | 0.00 | 0.00 | 0.00 |
| 24 | 8.63 | 1.13 | 5.60 | 2.22 | 8.02 | 0.91 |
| 48 | 134.64 | 58.32 | 54.84 | 19.63 | 55.17 | 23.76 |
| 72 | 439.83 | 180.61 | 200.08 | 18.44 | 177.48 | 66.82 |
| 96 | 607.17 | 175.95 | 491.54 | 86.19 | 363.03 | 71.53 |

OA: Oleic Acid
LA: Lauric Acid
IPM: Isopropyl Myristate
GMDC: Glycerol mono di Caprylate Graphic 15 of FIG. 10 shows the data of Table XII.

The cumulative amount of norethindrone acetate permeated is reported vs. time (h).

The curve marked with ● is obtained by using the patches which adhesive matrix has the composition disclosed in Example 4 (OALA).

The ■ curve shows the results obtained by using the adhesive matrix described in Example 8 (IPM).

The ▲ curve is obtained from the adhesive matrix disclosed in Example 9 (GMDC).

TABLE XIII

| | Estradiol Permeated (μg/sqcm) | | | | | |
|---|---|---|---|---|---|---|
| Time | Example 4 (OA/LA) | | Example 17 (OAL/LA) | | Example 18 (OAL/LAL) | |
| (h) | Mean | SEM | Mean | SEM | Mean | SEM |
| 0 | 0.00 | 0.00 | 0.00 | 0.00 | 0.00 | 0.00 |
| 24 | 1.99 | 0.29 | 1.95 | 0.23 | 2.09 | 0.47 |
| 48 | 11.00 | 0.95 | 9.29 | 1.19 | 10.88 | 1.82 |
| 72 | 31.72 | 5.29 | 21.31 | 1.75 | 38.32 | 7.82 |
| 96 | 63.44 | 5.93 | 55.20 | 11.32 | 75.61 | 12.96 |

OA: Oleic Acid
LA: Lauric Acid
OAL: Oleyl Alcohol
LAL: Lauryl Alcohol

Graphic 16 of FIG. 10 shows the data of Table XIII.

The cumulative amount of estradiol permeated ($\mu g/cm^2$) is reported vs. time (h).

The curve marked with ● is obtained by using the patches which adhesive matrix has the composition disclosed in Example 4 (OA/LA).

The ■ curve shows the results obtained by using the adhesive matrix having the composition disclosed in Example 17 (OAL/LA).

The ▲ curve shows the results obtained by using the adhesive matrix described in Example 18 (OAL/LAL).

TABLE XIV

| | Norethindrone Acetate Permeated (μg/sqcm) | | | | | |
|---|---|---|---|---|---|---|
| Time | Example 4 (OA/LA) | | Example 17 (OAL/LA) | | Example 18 (OAL/LAL) | |
| (h) | Mean | SEM | Mean | SEM | Mean | SEM |
| 0 | 0.00 | 0.00 | 0.00 | 0.00 | 0.00 | 0.00 |
| 24 | 4.36 | 0.51 | 3.47 | 0.66 | 4.83 | 1.15 |
| 48 | 26.46 | 2.38 | 27.61 | 7.46 | 55.57 | 17.19 |
| 72 | 147.06 | 42.39 | 105.65 | 20.13 | 269.82 | 53.54 |
| 96 | 356.28 | 44.00 | 335.28 | 104.27 | 501.16 | 68.48 |

OA: Oleic Acid
LA: Lauric Acid
OAL: Oleyl Alcohol
LAL: Lauryl Alcohol

Graphic 17 of FIG. 11 represents the values reported in Table XIV.

The cumulative amount of norethindrone acetate permeated ($\mu g/cm^2$) is reported vs. time (h).

The curve marked with ● is obtained from patches which adhesive matrix has the composition disclosed in Example 4 (OA/LA).

The ■ curve shows the results obtained by using the adhesive matrix that has the composition disclosed in Example 17 (OAL/LA).

The ▲ curve shows the results obtained from the adhesive matrix with the composition described in Example 18 (OAL/LAL).

TABLE XV

| | Estradiol permeated (μg/sqcm) | | | |
|---|---|---|---|---|
| Time | Example 4 (OA/LA) | | Example 7 (OA) | |
| (h) | Mean | SD | Mean | SD |
| 0 | 0.00 | 0.00 | 0.00 | 0.00 |
| 24 | 5.25 | 0.43 | 0.00 | 0.00 |
| 48 | 8.19 | 0.87 | 6.07 | 1.30 |
| 72 | 51.12 | 8.16 | 27.60 | 4.27 |
| 96 | 104.01 | 8.91 | 50.53 | 5.30 |

OA: Oleic Acid
LA: Lauric Acid

Graphic 18 of FIG. 11 shows the data of Table XV.

The cumulative amount of estradiol permeated ($\mu g/cm^2$) is reported vs. time (h).

The curve marked with Δ is obtained by using the patches which adhesive matrix has the composition disclosed in Example 4 (OA/LA).

The □ curve shows the results obtained from patches which adhesive matrix has the composition described in Example 7 (OA).

TABLE XVI

| | Norethindrone Acetate permeated (μg/sqcm) | | | |
|---|---|---|---|---|
| Time | Example 4 (OA/LA) | | Example 7 (OA) | |
| (h) | Mean | SD | Mean | SD |
| 0 | 0.00 | 0.00 | 0.00 | 0.00 |
| 24 | 4.49 | 0.36 | 1.98 | 0.18 |
| 48 | 27.62 | 7.91 | 9.80 | 0.25 |
| 72 | 207.57 | 56.51 | 59.07 | 25.06 |
| 96 | 558.56 | 53.14 | 139.29 | 45.50 |

OA: Oleic Acid
LA: Lauric Acid

The Graphic 19 in FIG. 12 shows the data of Table XVI.

The cumulative amount of norethindrone acetate ($\mu g/cm^2$) is reported vs. time (h).

The curve indicated with Δ is obtained by using the patches which adhesive matrix has the composition disclosed in Example 4 (OA/LA).

The □ curve shows the results obtained by using the adhesive matrix described in Example 7 (OA).

TABLE XVII

| | Permeated drug cumulative amount (μg/cm²) | | | | | |
|---|---|---|---|---|---|---|
| Time | Example 35 (OA/LA) Levonorgestrel | | Example 36 (OA/LA) Alprazolam | | Example 37 (OA/LA) Testosterone | |
| (h) | Mean | SD | Mean | SD | Mean | SD |
| 0 | 0.00 | 0.00 | 0.00 | 0.00 | 0.00 | 0.00 |
| 24 | 3.61 | 0.59 | 49.84 | 17.18 | 16.90 | 6.05 |
| 48 | 7.71 | 1.52 | 287.07 | 23.44 | 41.21 | 9.78 |
| 72 | 13.69 | 2.61 | 496.17 | 42.50 | 73.24 | 15.82 |
| 96 | — | — | 631.83 | 26.17 | 109.82 | 20.17 |

The Graphic 20 in FIG. 13 shows the data of Table XVII.

The cumulative amount of permeated Levonorgestrel ($\mu g/cm^2$) is reported vs. time (h).

The curve indicated with □ is obtained by using the patches which adhesive matrix has the composition disclosed in Example 35 (OA/LA).

The Graphic 21 of FIG. 13 shows the data of Table XVII.

The cumulative amount of permeated Alprazolam ($\mu g/cm^2$) is reported vs. time (h).

The curve indicated with □ is obtained by using the patches which adhesive matrix has the composition disclosed in Example 36 (OA/LA).

The Graphic 22 of FIG. 13 shows the data of Table XVII.

The cumulative amount of permeated of Testosterone ($\mu g/cm^2$) is reported vs. time (h).

The curve indicated with □ is obtained by using the patches which adhesive matrix has the composition disclosed in Example 37 (OA/LA).

Human Wearing Test

The aim of the study was to evaluate the adhesive properties of some prototypes in order to demonstrate the behavior and action of the cohesion improvers.

There are different in vitro methods to determine these specific properties. However any correlation or extrapolation of these properties to practical applications on human skin should not be made. For this reason it is advisable to perform human wearing test.

The evaluation of the main pressure-sensitive adhesives (PSA) properties are three basis properties: peel adhesion, tack and shear strength (cohesion).

Every application requires a different combination of these properties, taken into account that the improvement of one property must be carefully balanced against the possible destruction or deterioration of another.

As it was previously described, adding enhancers to PSA will plasticize the PSA and lower their shear strength. The reduction in shear resistance may result in adhesive residue on the skin (cohesion failure), edge lifting of the patch during wear, or loss of adhesion. The maintenance of adequate adhesive physical properties is particularly important for long periods of application.

Adhesive properties performance as well as the local tolerance were tested on 11 volunteers after a single application of each patch for 3 days. Each volunteer was observed every 24 hours. For each formulation the following evaluations were performed on the 11 volunteers:

| Adhesion Properties: | Skin Tolerance: |
|---|---|
| -Adhesion | -Erythema |
| -Edge Adhesive Residue (during the use of the patch) | -Edema |
| -Adhesive Transfer after Patch Removal | -Pruritus |

In "adhesion properties", the overall behavior of all properties (cohesion, adhesion and tack) were evaluated. Cohesion is the ability of the adhesive to resist splitting, therefore good cohesion is necessary for clean removal (non adhesive transfer after patch removal). Cold flow, adhesion and tack are specially evaluated by considering the adhesion and edge adhesive residue during the use of the patch.

Respect to "skin tolerance", erythema, edema and pruritus were specially evaluated. The results obtained are described in Table XVIII and Table XIX. Mean values of the volunteers after 72 hours of the use of the patches are included in each table.

TABLE XVIII

Adhesion test results

| | Composition (%) | | | | | |
|---|---|---|---|---|---|---|
| Batch N° | PSA | Ethyl Cellulose | Foral 105 E | Adhesion* | Edge Adhesive Residue** | Adhesive Transfer (Removal)*** |
| Pbo. 03 | 63.62 | — | 12.0 | 90% | 3 | 20% |
| Pbo. 16 | 63.45 | 0.5 | 12.0 | 100% | 2 | 20% |
| Pbo. 17 | 61.72 | 2.5 | 12.0 | 100% | 2 | 10% |
| Pbo. 12 | 54.00 | 10.0 | 12.0 | 100% | 0 | 0% |
| Pbo. 10 | 53.09 | — | 24.0 | 90% | 3 | 30% |
| Pbo. 19 | 52.93 | 0.5 | 24.0 | 100% | 2 | 20% |
| Pbo. 13 | 46.97 | 5.0 | 24.0 | 95% | 1 | 10% |
| Pbo. 09 | 43.09 | 10.0 | 24.0 | 100% | 1 | 0% |
| Pbo. 11 | 75.35 | — | — | 0% | — | — |
| Pbo. 08 | 65.86 | 10.0 | — | 85% | 0 | 0% |

All the batches contain BHT and BHA as antioxidant (0,03%/0,04%), Oleic Acid 12% and Lauric Acid 12%.
The PSA is Duro Tak 87-2852 in all batches.
*Adhesion was scored from 0 to 100% according to the surface of the patch adhered to the skin during the use of the patch.
**Edge adhesive residue was scored from 0 to 4 according to the width (quantity) of edge residue left on the skin during the use of the patch.
***Adhesive transfer (removal) refers to the transfer of adhesive from its normal position on the patch to the surface to which the patch was attached, either during removal. It was scored from 0 to 100% of the adhesive of the total patch that was transferred.

TABLE XIX

Skin reaction test results

| | Composition (%) | | | | | |
|---|---|---|---|---|---|---|
| Batch N° | PSA | Ethyl Cellulose | Foral 105 E | Erythema | Edema | Pruritus |
| Pbo. 3 | 63.62 | — | 12.0 | 0 | 0 | 0 |
| Pbo. 16 | 63.45 | 0.5 | 12.0 | 0 | 0 | 0 |
| Pbo. 17 | 61.72 | 2.5 | 12.0 | 2 | 0 | 0 |
| Pbo. 12 | 54.00 | 10.0 | 12.0 | 0 | 0 | 0 |
| Pbo. 10 | 53.09 | — | 24.0 | 0 | 0 | 0 |
| Pbo. 19 | 52.93 | 0.5 | 24.0 | 0 | 0 | 0 |
| Pbo. 13 | 46.97 | 5.0 | 24.0 | 0 | 0 | 0 |
| Pbo. 9 | 43.09 | 10.0 | 24.0 | 0 | 0 | 1 |
| Pbo. 11 | 75.35 | — | — | — | — | — |
| Pbo. 8 | 65.86 | 10.0 | — | 0 | 0 | 1 |

All the batches contain BHT and BHA as antioxidant (0,03%/0,04%), Oleic Acid 12% and Lauric Acid 12%.
The PSA is Duro Tak 87-2852 in all batches.
Observations were made immediately after the removal of the patches.
Erythema, Edema and Pruritus were scored from 0 to 4, where 0 means no reaction and 4 means severe reaction. In all cases, score 4 means withdrawal of the study.

17 β-estradiol and Norethindrone Acetate Bioavailability in Postmenopausal Women The estradiol and norethindrone acetate permeation rate achieved with a transdermal patch formulation containing said active agents was evaluated "in vivo" by measuring the estradiol and norethindrone serum levels in 12 postmenopausal women, applying one patch of 40 sqcm on the abdominal zone and removed after 7 days. Estragest TTS® was used as reference product. Estragest TTS® is a commercially available combination patch designed for 3 or 4 days use. Two Estragest TTS® were applied during the same treatment period. One patch was applied at the beginning of the treatment and removed on the 4th day and a second patch was applied to a different area of the abdomen and removed after 3 days to complete 7 day treatment.

The study was an open label, randomized, two-way crossover, comparative bioavailability study, conducted in 12 healthy postmenopausal women. The washout period was one month.

Venous blood samples were collected immediately prior to (basal value) and at 8, 24, 48, 72, 96, 120, 144, 168, 192 h after the application of our Combination Patch or the first Estragest TTS®.

Analytical assay method: estradiol and norethindrone serum levels were assayed using a radioimmuno-assay (RIA) method.

Tables XX and XXI and graphics 23 and 24 illustrate the results obtained.

Bioavailability Study Results

TABLE XX

| Serum levels of Estradiol (pg/ml) | | | | | | | | | |
|---|---|---|---|---|---|---|---|---|---|
| Time (h) | 0 | 8 | 24 | 48 | 72 | 96 | 120 | 144 | 168 | 192 |
| Mean | 16 | 38 | 54 | 61 | 55 | 55 | 51 | 46 | 47 | 20 |
| SEM | 2 | 6 | 5 | 5 | 5 | 6 | 6 | 4 | 6 | 2 |

TABLE XXI

| Serum levels of Norethindrone (pg/ml) | | | | | | | | | |
|---|---|---|---|---|---|---|---|---|---|
| Time (h) | 0 | 8 | 24 | 48 | 72 | 96 | 120 | 144 | 168 | 192 |
| Mean | 53 | 180 | 536 | 601 | 578 | 788 | 504 | 516 | 457 | 110 |
| SEM | 1 | 33 | 99 | 104 | 114 | 204 | 91 | 78 | 74 | 21 |

Steady state for estradiol level is achieved since 8 h for our Combination Patch, whilst for Estragest TTS® the estradiol serum concentration reaches a plateau at 48 h and in both cases are maintained up to 168 h.

The mean estradiol serum concentration during the steady state is 50 and 53 pg/ml for our Combination Patch and Estragest TTS®, respectively.

Steady state for norethindrone is achieved since 24 h for our Combination Patch (24 to 168 h), whilst for Estragest TTS® treatment the steady state is reached at 48 h until 168 h of treatment.

The mean norethindrone serum concentration at steady state is 569 and 663 pg/ml, for our Combination Patch and Estragest TTS®, respectively.

As it is clearly observed our patch formulation provides faster and sustained transdermal delivery of active agent(s), by virtue of the enhancer combination herein claimed (see FIG. 14).

By means of the invention herein claimed the in vitro drug permeation results demonstrated that higher and sustained drug permeation rate is achieved.

As it was previously asserted in in vitro and in vivo release studies, the differential release behaviour herein demonstrated by the fatty acids or fatty alcohols of different chain length, allow us to formulate and design monolithic transdermal systems with optimised drug permeation rate. Furthermore, human wearing test results denote a general improvement in the adhesive performance and especially in the cohesive strength of the adhesive in patches containing increased quantities of ethylcellulose. That is proved by the reduction in adhesive transfer after patch removal and by the reduction in the edge residue left onto the skin during use and after the removal of the patches. Also, no significant erythema, edema and pruritus were observed in any case (good tolerance). In conclusion, it has been discovered that the addition of cellulose derivatives as ethylcellulose and the addition of tackifier resin(s), could improve and recover the good performance of the adhesive properties.

Moreover, the bioavailability study results corroborate the in vitro drug permeation results demonstrating that the formulation claimed by us is useful for administering active agents by transdermal route during long periods of time. Providing faster and sustained drug plasmatic levels. Thus it is possible to achieve drug steady state values in shorter time and maintains this condition for longer period of time.

Therefore, the invention herein claimed can be used to achieve sustained controlled and adequate plasmatic levels of drug(s) throughout long periods of time, up to seven days, by virtue of our enhancer formulation and good adhesive properties, by mean of the addition of a cohesive improver.

What is claimed is:

1. A controlled release, monolithic patch for transdermal administration of drugs consisting essentially of:
    A) a flexible backing layer, substantially impermeable to a drug which is to be transdermally administered, said flexible backing layer comprising a film of a polymer selected from the group consisting of polyethylene, polypropylene, polyurethane, polyesters and polyethylene terephthalate, optionally laminated with aluminum foil,
    B) an adhesive layer comprising:
        (i) a pressure sensitive adhesive polymeric matrix, in an amount of 20% to 85% by weight of the total weight of the adhesive layer, said adhesive polymeric matrix being selected from the group consisting of cross-linked or not cross-linked copolymers of acrylic acid esters with vinyl acetate, silicone resins and polyisobutylene;
        (ii) ethylcellulose as a cohesive improver in an amount of 0.1% to 5% by weight of the total weight of the adhesive layer;
        (iii) a tackifier agent in an amount of 5% to 25% by weight of the total weight of the adhesive layer, said tackifier agent being selected from the group consisting of qlycerol esters of rosin, pentaereythritol esters of rosin, glycerol esters of hydrogenated rosin and pentaerythritol esters of hydrogenated rosin;
        (iv) a combination of permeation enhancers consisting of a first component in an amount from 3% to 18% by weight of the adhesive layer, said first component being a saturated fatty acid or fatty alcohol represented by the formula $CH_3-(CH_2)_n-COOH$ or $CH_3-(CH_2)_n-CH_2OH$ in which n is an integer from 6 to 16, and of a second component in an amount of from 3% to 18% of the layer which is a monounsaturated fatty acid or fatty alcohol of the formula $CH_3-C_nH_{2(n-1)}-COOH$ or $CH_3-C_nH_{2(n-1)}-CH_2OH$ respectively, in which n is an integer from 8 to 22, with the proviso that the chain length of the first component is different from that of the second component; and
        (v) one or more drugs as the active agent, in an amount from 0.5% to 15% by weight, which are dissolved or microdispersed in the adhesive layer; and
    C) a protective liner disposed over the adhesive layer, said protective liner being removable at the moment of use.

2. A patch for transdermal administration according to claim 1 wherein the protective liner (C) consists of a polyethylene or polyester film coated with a layer of silicone.

3. A patch for transdermal administration of drugs according to claim 1 wherein the protective liner C) consists of polyethylene or a polyester film coated with a layer of silicone.

4. A patch for transdermal administration of drugs according to claim 1 wherein the enhancer combination consists of lauric acid or lauryl alcohol in an amount of 3% to 18% by weight with respect to the total weight of the adhesive layer and of oleic acid or oleyl alcohol in the amount of 3% to 18% by weight with respect to the total weight of the adhesive layer.

* * * * *